US011771321B2

(12) United States Patent
Pan et al.

(10) Patent No.: US 11,771,321 B2
(45) Date of Patent: Oct. 3, 2023

(54) SYSTEM, METHOD, AND COMPUTER-ACCESSIBLE MEDIUM FOR SUBSURFACE CAPILLARY FLOW IMAGING BY WAVELENGTH-DIVISION-MULTIPLEXING SWEPT-SOURCE OPTICAL DOPPLER TOMOGRAPHY

(71) Applicant: THE RESEARCH FOUNDATION FOR THE STATE UNIVERSITY OF NEW YORK, Albany, NY (US)

(72) Inventors: Yingtian Pan, Stony Brook, NY (US); Wei Chen, Stony Brook, NY (US); Congwu Du, Stony Brook, NY (US)

(73) Assignee: The Research Foundation for SUNY, Albany, NY (US)

( * ) Notice: Subject to any disclaimer, the term of this patent is extended or adjusted under 35 U.S.C. 154(b) by 395 days.

(21) Appl. No.: 16/755,702

(22) PCT Filed: Oct. 12, 2018

(86) PCT No.: PCT/US2018/055680
§ 371 (c)(1),
(2) Date: Apr. 13, 2020

(87) PCT Pub. No.: WO2019/075376
PCT Pub. Date: Apr. 18, 2019

(65) Prior Publication Data
US 2021/0196126 A1 Jul. 1, 2021

Related U.S. Application Data

(60) Provisional application No. 62/571,845, filed on Oct. 13, 2017.

(51) Int. Cl.
*A61B 5/00* (2006.01)
*A61B 5/026* (2006.01)
(Continued)

(52) U.S. Cl.
CPC .............. *A61B 5/0066* (2013.01); *A61B 3/10* (2013.01); *A61B 3/102* (2013.01); *A61B 5/0075* (2013.01);
(Continued)

(58) Field of Classification Search
CPC ..... A61B 5/0066; A61B 5/0075; A61B 5/026; A61B 3/102; A61B 3/10; G01B 9/02004;
(Continued)

(56) References Cited

U.S. PATENT DOCUMENTS 6,549,801 B1 4/2003 Chen et al.
7,782,464 B2 8/2010 Mujat et al.
(Continued)

FOREIGN PATENT DOCUMENTS

CN 105796053 A 7/2016
CN 106943124 B * 7/2020 ........... A61B 3/0025
(Continued)

OTHER PUBLICATIONS

International Search Report for International Patent Application No. PCT/US2018/055680 dated Feb. 4, 2019.
(Continued)

*Primary Examiner* — Dominic J Bologna
(74) *Attorney, Agent, or Firm* — ACKNOWLEDGE IP P.C.; Paul Ackerman

(57) ABSTRACT

An exemplary system, method, and computer-accessible medium for generating an image(s) of an three-dimensional anatomical flow map(s) can include receiving an optical coherence tomography ("OCT") signal(s), splitting the OCT signal(s) into a plurality of subspectra, averaging the plurality of subspectra, and generating the image(s) of the three-dimensional anatomical flow map(s) based on the averaged subspectra. The OCT signal(s) can be a swept-source OCT signal. The OCT signal(s) can be split into the
(Continued)

subspectra based on a Hamming window. The Hamming distance window can be optimized to minimize a nearest side lobe for each of the subspectra. A position of at least one of the subspectra can be shifted prior to averaging the subspectra. The position of all but one of the subspectra can be shifted prior to averaging the subspectra.

21 Claims, 17 Drawing Sheets

(51) Int. Cl.
   G01B 9/02004 (2022.01)
   G01B 9/02 (2022.01)
   G01B 9/02091 (2022.01)
   G01B 9/02015 (2022.01)
   G01B 9/02055 (2022.01)
   A61B 3/10 (2006.01)
   G06T 7/00 (2017.01)

(52) U.S. Cl.
   CPC .......... A61B 5/026 (2013.01); G01B 9/02004 (2013.01); G01B 9/02027 (2013.01); G01B 9/02044 (2013.01); G01B 9/02075 (2013.01); G01B 9/02083 (2013.01); G01B 9/02091 (2013.01); G06T 7/0012 (2013.01); G06T 2207/10101 (2013.01); G06T 2207/20056 (2013.01); G06T 2207/30104 (2013.01)

(58) Field of Classification Search
   CPC ............ G01B 9/02044; G01B 9/02083; G01B 9/02091; G01B 9/02027; G01B 9/02075; G06T 2207/10101; G06T 2207/20056; G06T 2207/30104; G06T 7/0012
   See application file for complete search history.

(56) References Cited

U.S. PATENT DOCUMENTS

| 7,917,312 | B2 | 3/2011 | Wang et al. |
| 8,081,808 | B2 | 12/2011 | Huang et al. |
| 8,135,453 | B2 | 3/2012 | Slabaugh et al. |
| 8,175,685 | B2 | 5/2012 | Yun et al. |
| 8,244,334 | B2 | 8/2012 | Huang et al. |
| 8,401,246 | B2 | 3/2013 | Huang et al. |
| 8,721,077 | B2 | 5/2014 | Vermeer et al. |
| 9,025,159 | B2 | 5/2015 | Huang et al. |
| 9,060,689 | B2 | 6/2015 | Tearney et al. |
| 9,226,660 | B2 | 1/2016 | De Boer et al. |
| 9,307,926 | B2 | 4/2016 | Begin et al. |
| 9,324,141 | B2 | 4/2016 | Begin |
| 9,713,424 | B2 | 7/2017 | Spaide |
| 9,795,301 | B2 | 10/2017 | Fleming et al. |
| 9,844,315 | B2 | 12/2017 | Chen et al. |
| 9,883,810 | B2 | 2/2018 | Jia et al. |
| 9,962,075 | B2 | 5/2018 | Liu et al. |
| 9,978,159 | B2 | 5/2018 | Kraus et al. |
| 10,186,056 | B2 | 1/2019 | Senzig et al. |
| 10,213,100 | B2 | 2/2019 | Takeno et al. |
| 10,299,682 | B1 | 5/2019 | Yang et al. |
| 10,335,026 | B2 | 7/2019 | Inao et al. |
| 10,354,378 | B2 | 7/2019 | Wang et al. |
| 10,426,337 | B2 | 10/2019 | Chong |
| 10,480,926 | B2 | 11/2019 | Froggatt et al. |
| 10,485,423 | B2 | 11/2019 | Huang et al. |
| 10,559,388 | B2 | 2/2020 | Lavi et al. |
| 10,575,723 | B2 | 3/2020 | Kagemann, Jr. et al. |
| 10,702,146 | B2 | 7/2020 | Raymond et al. |
| 10,729,327 | B2 | 8/2020 | Adamson et al. |
| 10,758,122 | B2 | 9/2020 | Spaide |
| 10,776,988 | B2 | 9/2020 | Grady et al. |
| 10,800,831 | B2 | 10/2020 | Yun |
| 10,885,630 | B2 | 1/2021 | Li et al. |
| 11,060,843 | B2 | 7/2021 | Mohseni et al. |
| 11,096,585 | B2 | 8/2021 | Zhou et al. |
| 11,202,572 | B2 | 12/2021 | Mak et al. |
| 11,448,496 | B2 | 9/2022 | Ruan et al. |
| 11,490,817 | B2 | 11/2022 | Horstmeyer et al. |
| 11,501,485 | B2 | 11/2022 | Grady et al. |
| 2003/0208326 | A1 | 11/2003 | Chen et al. |
| 2007/0263277 | A1 | 11/2007 | Liang et al. |
| 2009/0225301 | A1 | 9/2009 | Morofke et al. |
| 2010/0141956 | A1 | 6/2010 | Leitgeb et al. |
| 2011/0170111 | A1 | 7/2011 | Rolland et al. |
| 2013/0289882 | A1 | 10/2013 | Sharma et al. |
| 2015/0148654 | A1 | 5/2015 | Whanwook et al. |
| 2016/0106319 | A1* | 4/2016 | Yasuno ................ A61B 5/0066 600/425 |
| 2016/0150954 | A1 | 6/2016 | Furuuchi et al. |
| 2016/0228000 | A1 | 8/2016 | Spaide et al. |
| 2016/0278629 | A1 | 9/2016 | Schuele |
| 2016/0287071 | A1* | 10/2016 | Tan ...................... A61B 3/0025 |
| 2016/0317020 | A1 | 11/2016 | Liu et al. |
| 2016/0331229 | A1* | 11/2016 | Huang ................. A61B 5/0066 |
| 2017/0074640 | A1* | 3/2017 | Cable ................. G01B 9/02007 |
| 2018/0192870 | A1 | 7/2018 | Inao et al. |
| 2018/0242844 | A1 | 8/2018 | Liu et al. |
| 2018/0256025 | A1 | 9/2018 | Liu et al. |
| 2018/0344149 | A1 | 12/2018 | Chong |
| 2019/0069849 | A1 | 3/2019 | Hendon et al. |
| 2019/0082952 | A1 | 3/2019 | Zhang et al. |
| 2019/0343383 | A1 | 11/2019 | Spaide |

FOREIGN PATENT DOCUMENTS

| EP | 2144566 | B1 | | 6/2014 | |
| EP | 2884223 | A1 | | 6/2015 | |
| EP | 2903533 | A1 | | 8/2015 | |
| EP | 3102090 | A1 | | 12/2016 | |
| EP | 3111833 | A1 | | 1/2017 | |
| EP | 2784438 | B1 | | 10/2018 | |
| JP | 2002503134 | A | * | 1/2002 | ........... A61B 5/0073 |
| JP | 2015511146 | A | * | 4/2015 | ............. A61B 3/102 |
| JP | 2016106652 | A | * | 6/2016 | ........... A61B 3/0025 |
| JP | 6200902 | B2 | * | 9/2017 | ............. A61B 3/102 |
| JP | 6240064 | B2 | * | 11/2017 | ............. A61B 3/102 |
| JP | 6402921 | B2 | * | 10/2018 | ........... A61B 3/0025 |
| TW | 569008 | B | | 1/2004 | |

OTHER PUBLICATIONS

International Written Opinion for International Patent Application No. PCT/US2018/055680 dated Feb. 4, 2019.

Dai et al., "Absolute Retinal Blood Flow Measurement with a Dual-Beam Doppler optical Coherence Tomography" IOVS, vol. 54, No. 13, pp. 7998-8003, Dec. 2013.

Makita et al., "Comprehensive in vivo micro-vascular imaging of the human eye by dual-beam-scan Doppler Optical Coherence Angiography" Optics Express, vol. 19, No. 2, pp. 1-13, Jan. 17, 2011.

Blatter et al., "Dove Prism based Rotating dual beam Bidirectional Doppler OCT," Biomedical Optics Express, vol. 4, No. 7, pp. 1-16, Jul. 1, 2013.

Mao et al., "Simultaneous Multi-Wavelength-Band Optical Frequency Domain Imaging for Spectroscopic Investigations" Proc. Of SPIE, pp. 1-7, vol. 8155.

\* cited by examiner

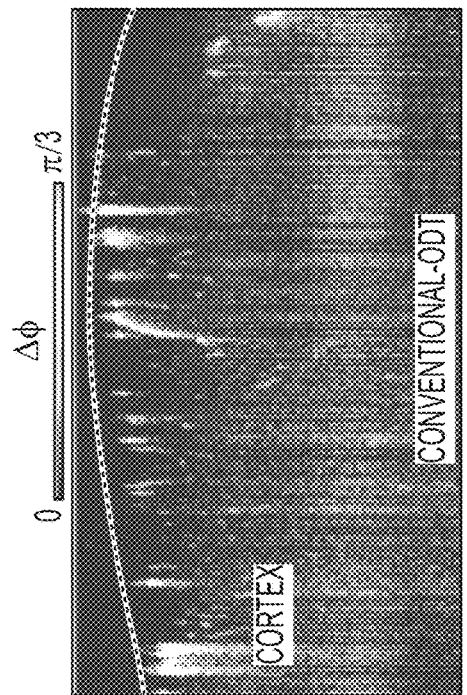
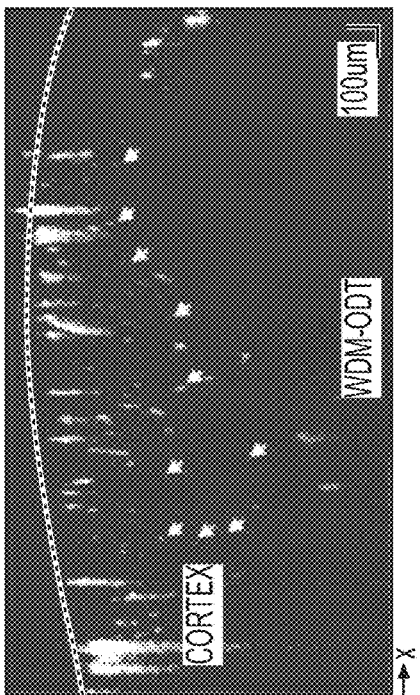
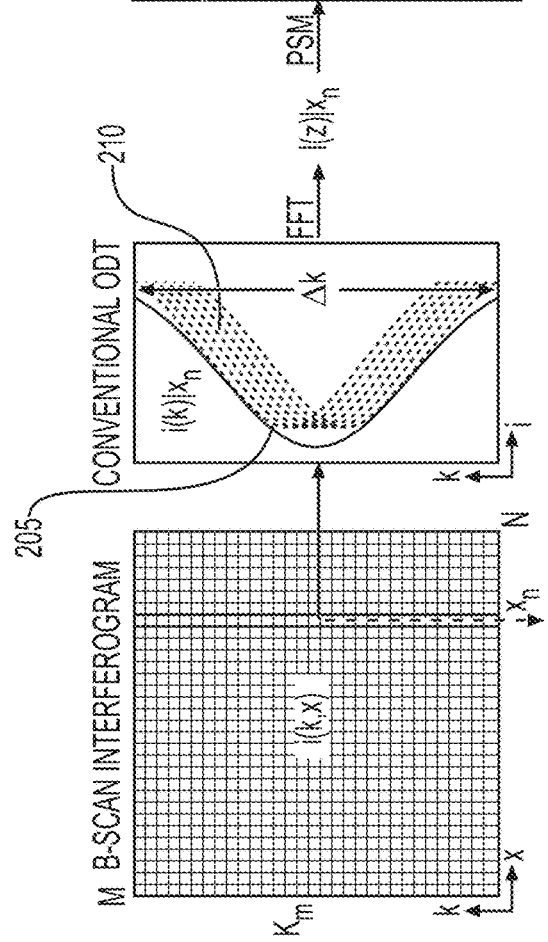
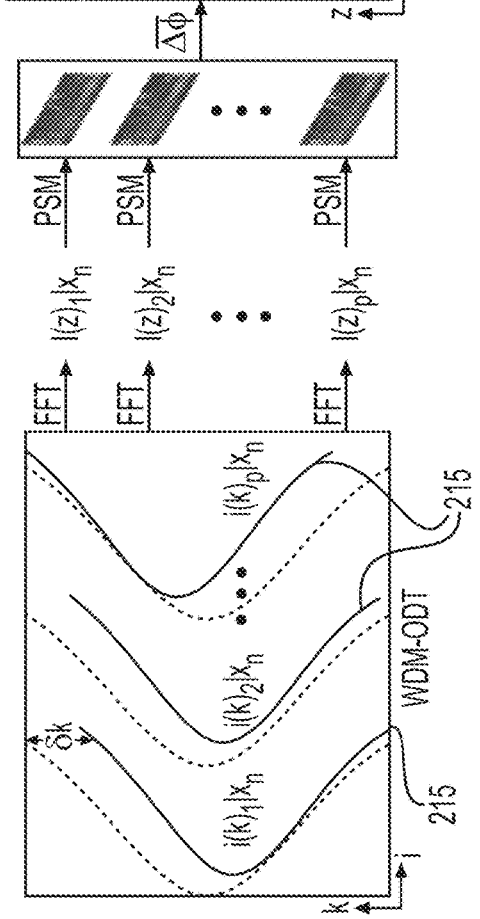

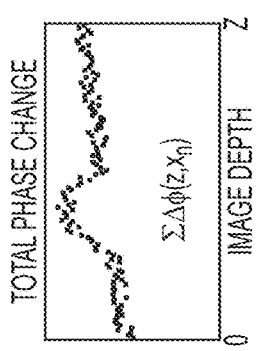
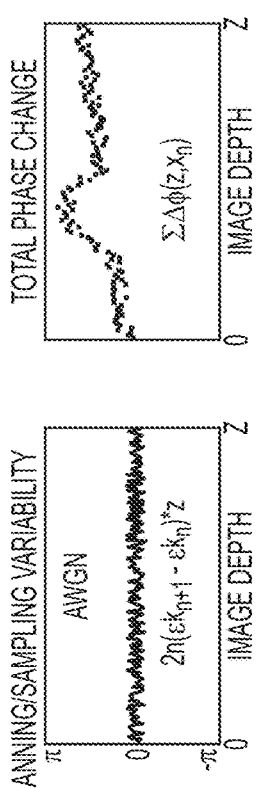
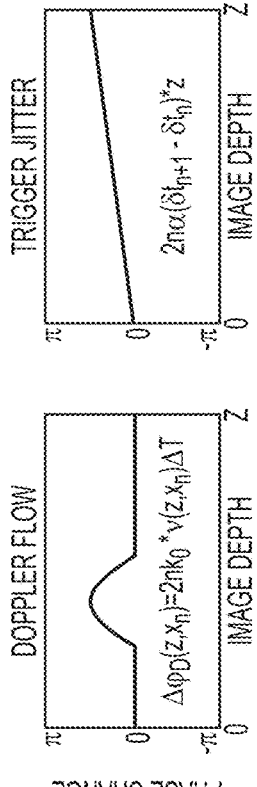
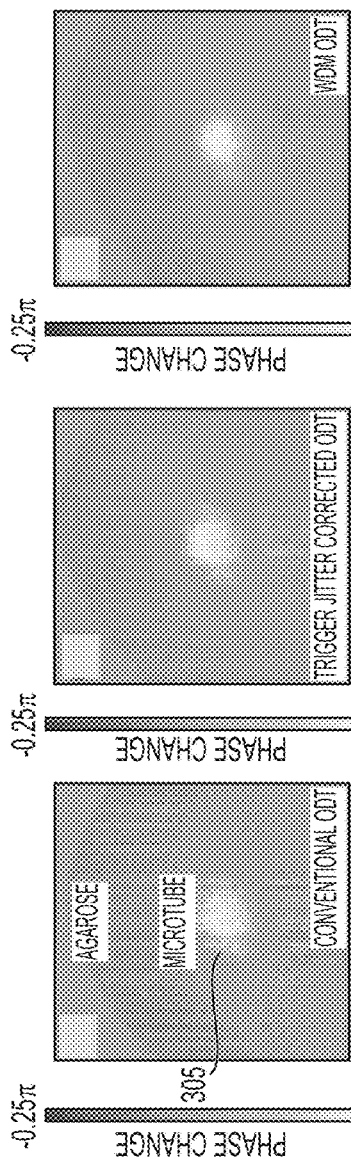
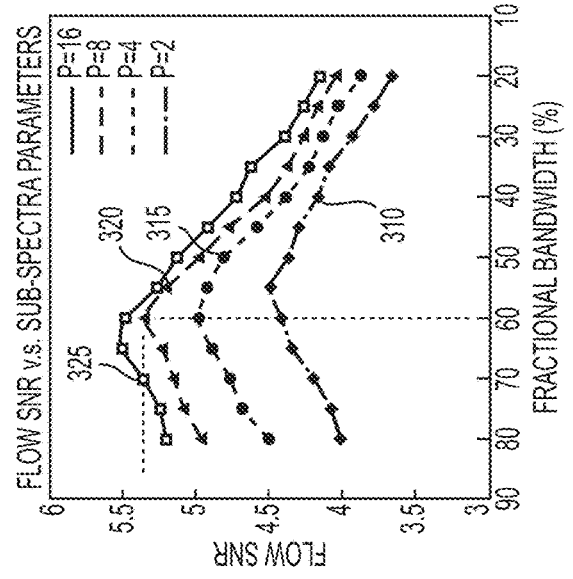
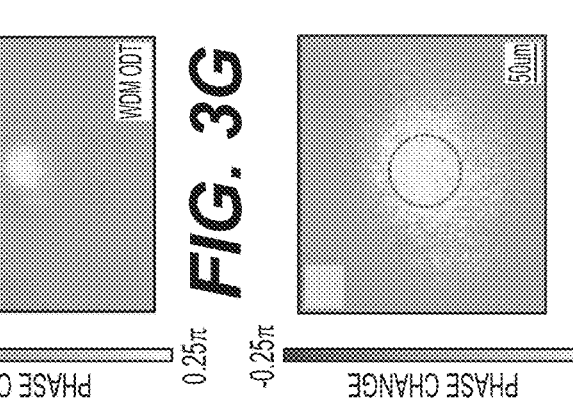

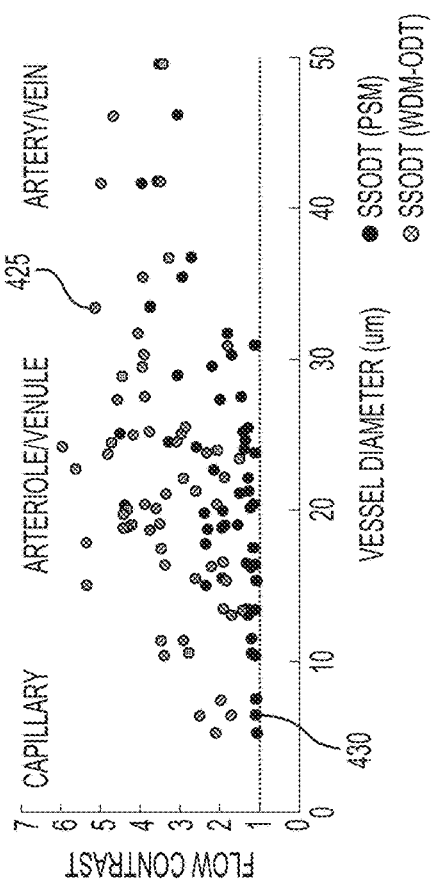
FIG. 4C FIG. 4D
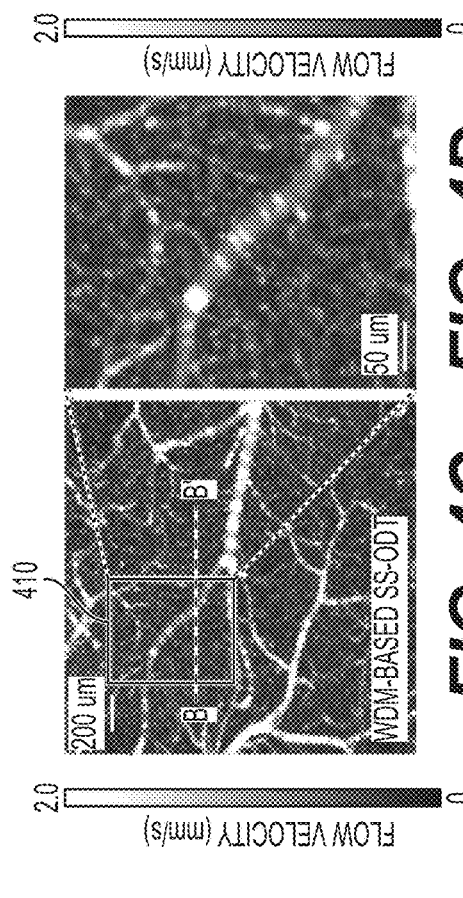
FIG. 4A FIG. 4B
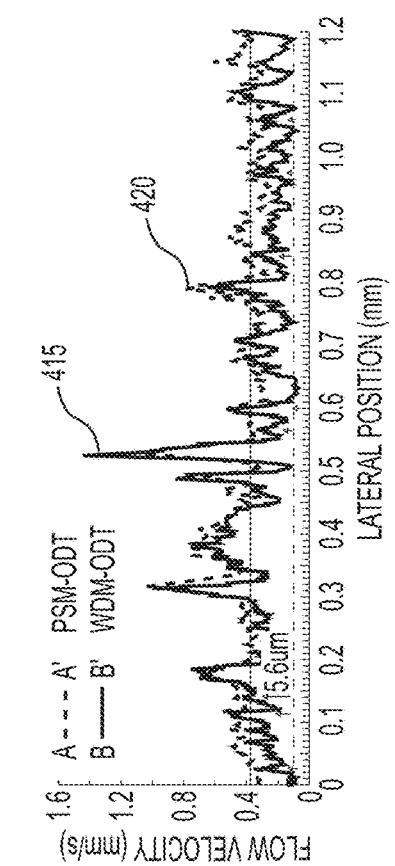
FIG. 4F
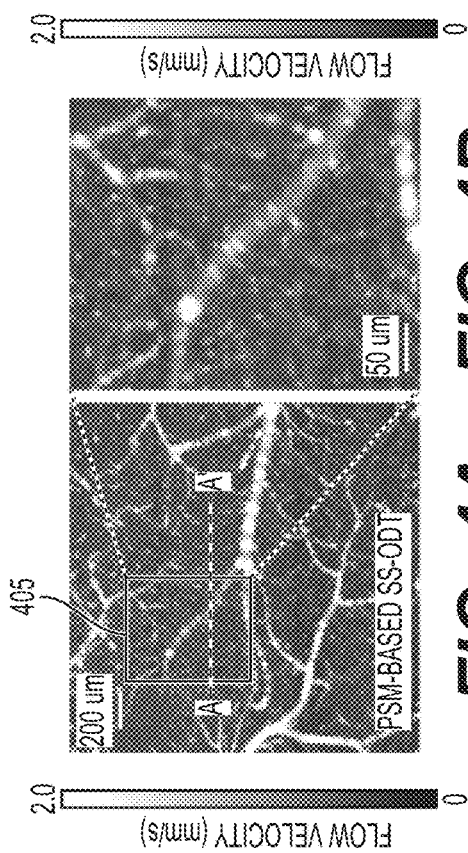
FIG. 4E

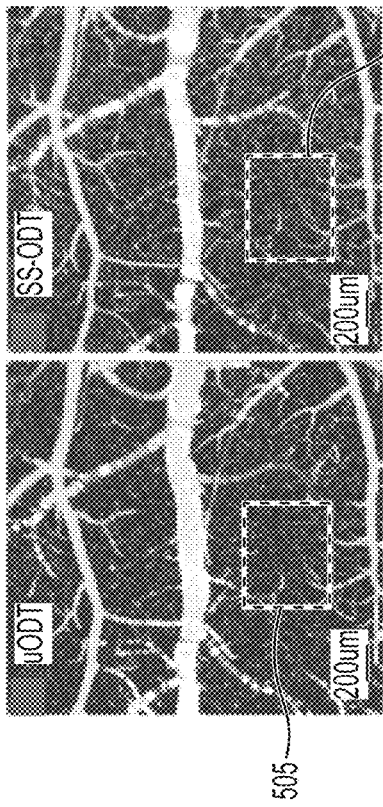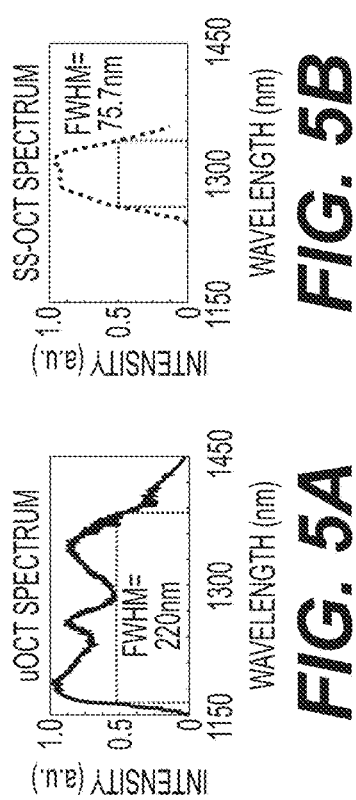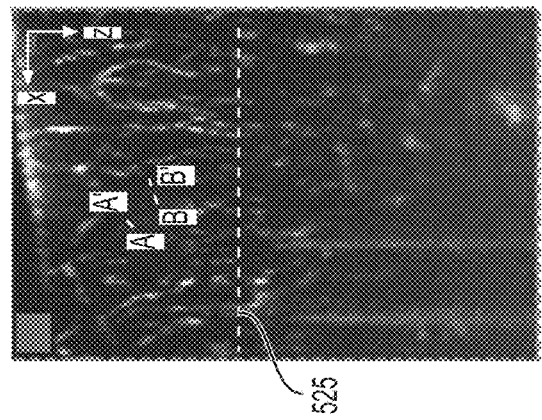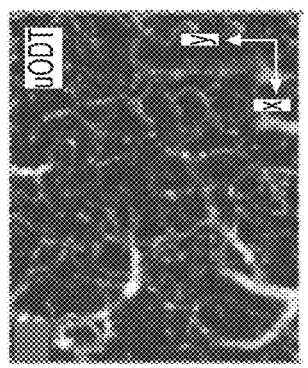
FIG. 5A  FIG. 5B  FIG. 5C  FIG. 5D  FIG. 5E  FIG. 5F

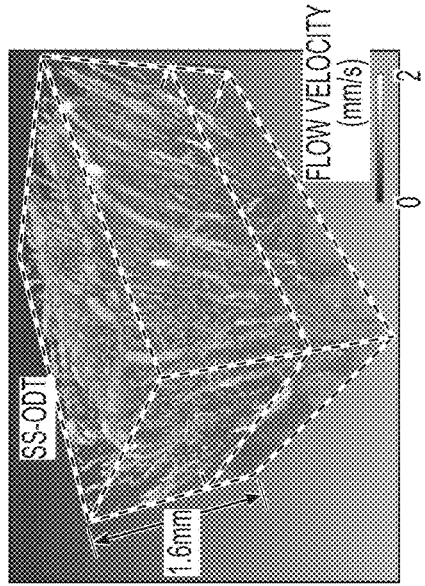
FIG. 6A
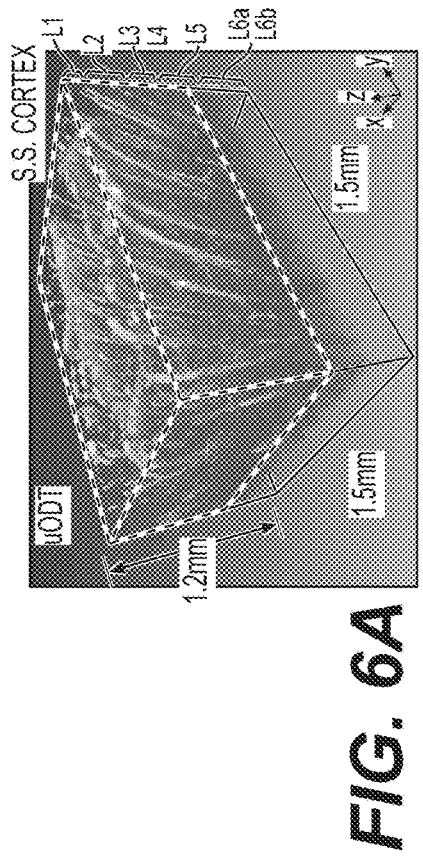
FIG. 6B
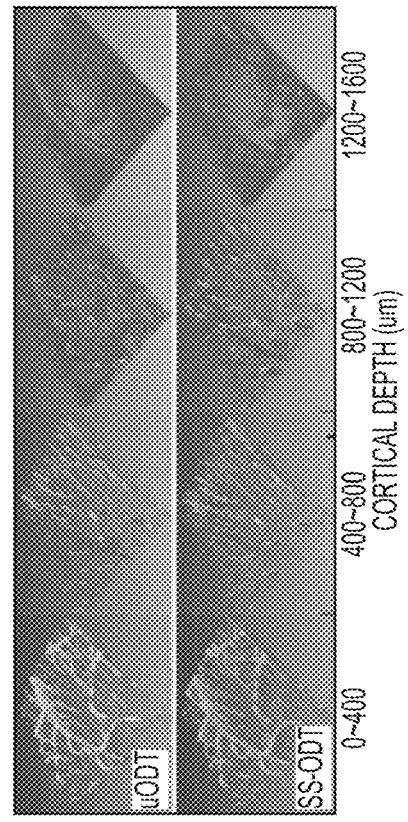
FIG. 6C
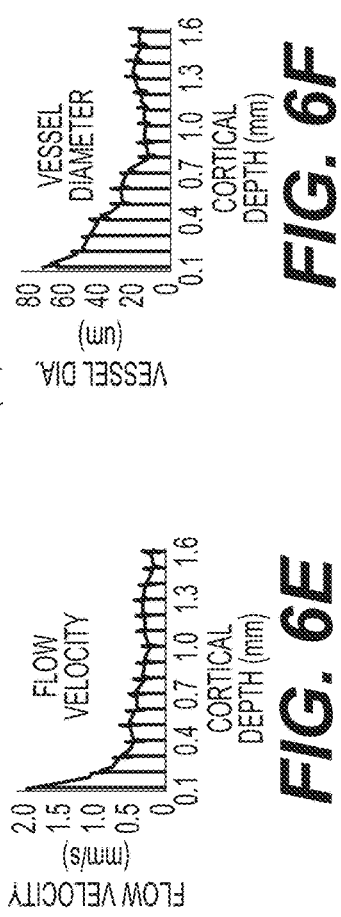
FIG. 6E
FIG. 6F
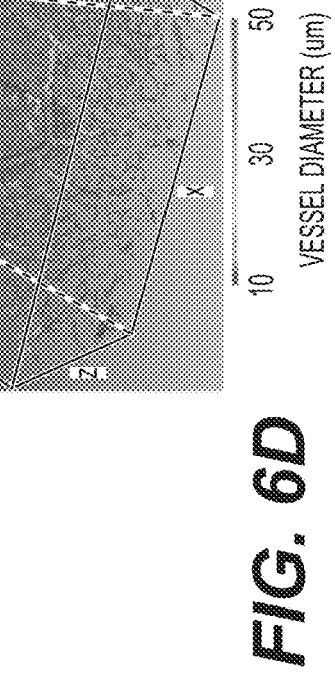
FIG. 6D

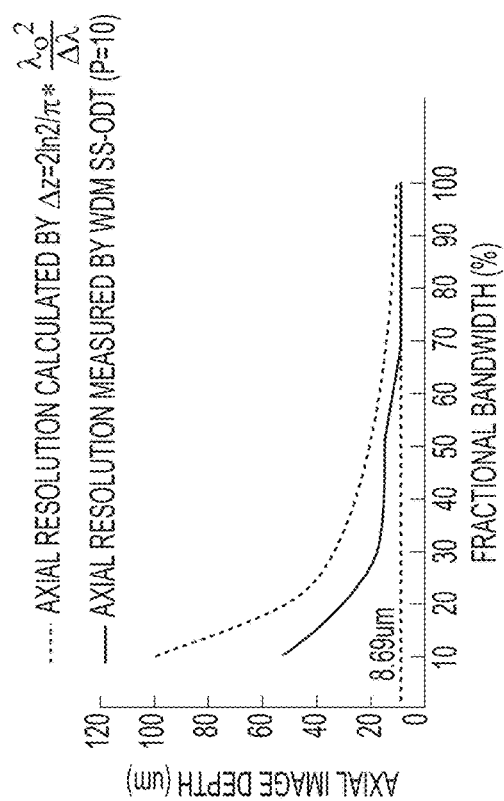
FIG. 9A
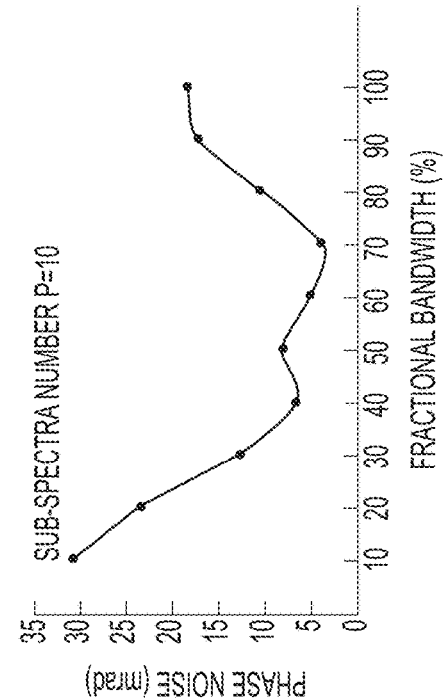
FIG. 9B
FIG. 9D
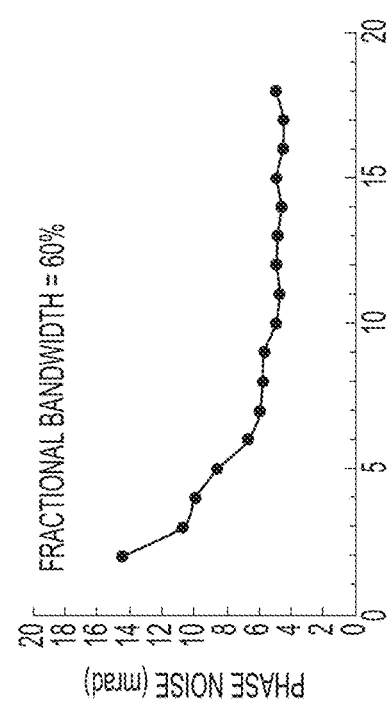
FIG. 9C

SYSTEM, METHOD, AND COMPUTER-ACCESSIBLE MEDIUM FOR SUBSURFACE CAPILLARY FLOW IMAGING BY WAVELENGTH-DIVISION-MULTIPLEXING SWEPT-SOURCE OPTICAL DOPPLER TOMOGRAPHY

CROSS REFERENCE TO RELATED APPLICATION(S)

This application claims priority to International Patent Application No. PCT/US2018/055680, filed Oct. 12, 2018, and published on Apr. 18, 2019 as International Publication No. WO 2019/075376 and relates to and claims priority from U.S. Provisional Patent Application No. 62/571,845, filed on Oct. 13, 2017, the entire disclosures of which are incorporated herein by reference.

STATEMENT REGARDING FEDERALLY SPONSORED RESEARCH

This invention was made with government support under Grant Nos. DA029718, DA042597, awarded by the National Institutes of Health. The government has certain rights in the invention.

FIELD OF THE DISCLOSURE

The present disclosure relates generally to medical imaging, and more specifically, to exemplary embodiments of a system, method, and computer-accessible medium for subsurface capillary flow imaging by swept-source optical Doppler tomography.

BACKGROUND INFORMATION

Optical coherence tomography ("OCT") has shown promise as an enabling biophotonic imaging technology for both preclinical studies (see, e.g., References 1-3), and clinical diagnoses. (See, e.g., Reference 4). Recent advances in functional OCT further broaden the potential applications from morphological imaging to quantitative 3D microcirculation imaging (see, e.g., References 5-7), tissue mechanical properties imaging (see, e.g., Reference 8), and contrast-enhanced molecular imaging (see, e.g., Reference 9), providing new ways to understand the biological systems. Optical Doppler tomography ("ODT"), as a functional variant of OCT, can provide 3D quantitative flow velocity of the blood flow, including cerebral blood flow ("CBFv"), without the need for contrast agents. (See, e.g., References 10 and 11). Compared to other technologies that have been used for microvascular imaging in the brain, such as laser speckle contrast imaging, 2-photon microscopy, and magnetic resonance angiography, ODT provides a balance between 3D imaging capability, large field of view, high spatial resolution for capillary flow imaging, and high temporal resolution for flow dynamics. These qualities have made ODT an attractive candidate for functional brain studies, such as a stroke (see, e.g., Reference 12), traumatic brain injury (see, e.g., Reference 13), drug addiction (see, e.g., Reference 14), and potentially tracking the hemodynamic response to brain activations. (See, e.g., Reference 15).

Currently, camera-based ultrahigh-resolution optical Doppler tomography ("uODT") is commonly used for quantitative capillary flow imaging due to its inherent high phase stability and superb axial resolution (e.g., approximately 2-3 μm) (see, e.g., Reference 6), whereas swept-source-based optical Doppler tomography ("SS-ODT") so far is rarely used for quantitative capillary flow imaging, for example, in cerebral cortex as a result of phase noise. However, since SS-ODT suffers less from sensitivity decay compared with uODT (see, e.g., Reference 16), it may be more suitable for flow imaging in deeper brain regions. In addition, the potential faster imaging speed of SS-ODT makes it more attractive for functional brain studies. Recent advances in swept sources, including vertical-cavity surface-emitting laser ("VCSEL") (see, e.g., Reference 17), Fourier-domain-mode-lock-laser (see, e.g., Reference 18), and akinetic swept lasers (see, e.g., Reference 19), have increased the A-scan speed into MHz, and the imaging range to several meters (see, e.g., Reference 20), offering various new prospects for biomedical applications. Additionally, some imaging methods have demonstrated microvascular even capillary imaging qualities using swept-source-based optical coherence tomography ("SS-OCT"), although the majority of approaches are based on the decorrelation of intensity signal, and only provide qualitative flow information. (See, e.g., Reference 21).

Efforts to facilitate SS-ODT for quantitative flow imaging have been reported with attempts to reduce the inherent high phase noises, including the calibration of trigger jitters-induced phase artifacts by adding common-path mirrors (see, e.g., Reference 22), by interferograms alignment in the spectral domain (see, e.g., Reference 14), and by numerical phase calibration methods. (See, e.g., Reference 23). While these methods have shown some improvements in flow detection sensitivity, few of the results provide the capillary flow imaging that uODT enables. A recent study of the phase noises in SS-OCT showed that except the trigger jitter-induced phase artifacts, the scanning variability of a swept source that introduced random phase noises also contribute to the background phase noise (see, e.g., Reference 24), which may be the limitation for ultrasensitive cerebral capillary flow imaging using SS-ODT.

Thus, it may be beneficial to provide an exemplary system, method, and computer-accessible medium for subsurface capillary flow imaging by wavelength-division-multiplexing swept-source optical Doppler tomography which can overcome at least some of the deficiencies described herein above.

SUMMARY OF EXEMPLARY EMBODIMENTS

An exemplary system, method, and computer-accessible medium for generating an image(s) of an three-dimensional anatomical flow map(s) can include receiving an optical coherence tomography ("OCT") signal(s), splitting the OCT signal(s) into a plurality of subspectra, averaging the plurality of subspectra, and generating the image(s) of the three-dimensional anatomical flow map(s) based on the averaged subspectra. The OCT signal(s) can be a swept-source OCT signal. The OCT signal(s) can be split into the subspectra based on a Hamming window. The Hamming distance window can be optimized to minimize a nearest side lobe for each of the subspectra. A position of at least one of the subspectra can be shifted prior to averaging the subspectra. The position of all but one of the subspectra can be shifted prior to averaging the subspectra.

In some exemplary embodiments of the present disclosure, the amount of the shift can be based on a number of the subspectra. The position can be shifted such that each of the subspectra has a same position. A bandwidth for a particular one of the subspectra can be a total bandwidth of the OCT signal(s) minus an amount of bandwidth lost based on a number of the subspectra. The OCT signal(s) can be split by shifting a filter across the OCT signal(s) using a particular step size. The particular step size can be an amount of bandwidth lost based on a number of the subspectra divided by a total number of the subspectra. The at least one image can include a blood flow.

In certain exemplary embodiments of the present disclosure, the OCT signal(s) can include at least two OCT signals. A first OCT signal of the at least two OCT signals can be into a plurality of first subspectra, a second OCT signal of the at least two OCT signals can be split into a plurality of second subspectra, a subspectra set can be generated by subtracting the first subspectra from the second subspectra, and the image(s) of the three-dimensional anatomical flow map(s) can be generated based on the subspectra set. An average of the subspectra set can be generated. The image(s) can be generated based on the averaged subspectra set.

A method for generating an image(s) of an three-dimensional anatomical flow map(s) can include simultaneously generating two radiation beams, providing the two radiation beams to the anatomical structure such that a temporal shift is created between the two radiation beams, receiving two return radiation beams from the three-dimensional anatomical flow map(s) that are based on the two radiation beams, and generating the image(s) by comparing the two return radiation beams. The temporal shift can be created by combining the two radiation beams into a single collinear beam, and splitting the single collinear beam. The two radiation beams can be combined using a polarization beam splitter. The single collinear beam can be split using a Wollaston prism.

A system for generating an image(s) of an three-dimensional anatomical flow map(s) can include a single swept source configured to generate two radiation beams, a polarization beam splitter configured to generate a single collinear beam based on the two radiation beams, and a prism configured to split the single collinear beam and provide first and second incident beams to the anatomical structure, said first and second incident beams having a temporal shift therebetween. The prism can be a Wollaston prism.

An exemplary system, method, and computer-accessible medium for generating an image(s) of an three-dimensional anatomical flow map(s) can include, receiving a first optical coherence tomography ("OCT") signal, receiving a second OCT signal, where the second OCT signal is temporally shifted from the first OCT signal, splitting the first OCT signal into a plurality of first subspectra, splitting the second OCT signal into a plurality of second subspectra, generating a subspectra set by subtracting the first subspectra from the second subspectra; averaging the subspectra set, and generating the image(s) of the three-dimensional anatomical flow map(s) based on the averaged subspectra set. A complete first OCT signal can be received prior to receiving the second OCT signal. The first OCT signal can be generated using a first output of a single swept-source and the second OCT signal can be generated using a second output of the single swept-source, and where the first output can be different from the second output.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 2A is a 2D matrix of a transverse B-scan interferogram;

FIG. 2B is a diagram of a phase subtraction method used to derive a cross-section Doppler flow map;

FIG. 2C is a conventional two-dimensional optical Doppler tomography image generated using a phase subtraction method;

FIG. 2D is a diagram illustrating an image where the full spectrum has been split into p phase-correlated subspectra according to an exemplary embodiment of the present disclosure;

FIG. 2E is a diagram illustrating averaging across a set of optical Doppler tomography images generated base on p-set of sub-spectral ODT according to an exemplary embodiment of the present disclosure;

FIG. 2F is a wavelength-dividing-multiplexing optical Doppler tomography map according to an exemplary embodiment of the present disclosure;

FIGS. 3A-3C are exemplary graphs illustrating a simulation of depth-dependent phase changes induced by moving scatterers to be measured and noises from swept source jittering and sweeping variability according to an exemplary embodiment of the present disclosure;

FIG. 3D is a graph illustrating a simulation of total phase change based on FIGS. 3A-3C according to an exemplary embodiment of the present disclosure;

FIGS. 3E-3G are exemplary images of a phantom flow reconstructed using a conventional approach, after correction of jitter noise, and then after correction of scanning variability noise;

FIGS. 3H-3J are exemplary images of the cross-sectional flow maps of FIGS. 3E-3G, respectively, according to an exemplary embodiment of the present disclosure;

FIG. 3K is a graph of the flow SNR measured using different subspectra according to an exemplary embodiment of the present disclosure;

FIGS. 4A and 4B are maximum intensity projection images according to an exemplary embodiment of the present disclosure;

FIGS. 4C and 4D are maximum intensity projection images generated using wavelength division multiplexing optical Doppler tomography according to an exemplary embodiment of the present disclosure;

FIG. 4E is a graph illustrating cross-sectional blood flow profiles according to an exemplary embodiment of the present disclosure;

FIG. 4F is a graph illustrating a comparison of flow contrasts for individual vessels shown in FIG. 4E, illustrating SNR improvement for flows in smaller vessels (e.g., capillaries) according to an exemplary embodiment of the present disclosure;

FIG. 5A is a graph illustrating power spectra of an ultra-broadband superluminescent diode according to an exemplary embodiment of the present disclosure;

FIG. 5B is a graph illustrating power spectra of a swept-source optical coherence tomography system according to an exemplary embodiment of the present disclosure;

FIG. 5C is an image produced using a ultra-broadband superluminescent spectral-domain optical coherence Doppler tomography according to an exemplary embodiment of the present disclosure;

FIG. 5D is an image produced using a swept-source optical coherence tomography system according to an exemplary embodiment of the present disclosure;

FIG. 5E is a zoomed in view of the image from FIG. 5C according to an exemplary embodiment of the present disclosure;

FIG. 5F is a side view image of the capillary network shown in FIG. 5E according to an exemplary embodiment of the present disclosure;

FIG. 6A is an image of an in vivo capillary network in a mouse cortex generated using a high resolution optical Doppler tomography system according to an exemplary embodiment of the present disclosure;

FIG. 6B is an image of an in vivo capillary network in a mouse cortex generated using a swept-source optical Doppler tomography system according to an exemplary embodiment of the present disclosure;

FIG. 6C is a set of images of a comparison of sectional 3D images of microvascular flow networks according to an exemplary embodiment of the present disclosure;

FIG. 6D is an image of the segmentation of the 3D microvascular flow network generated using a swept-source optical Doppler tomography system according to an exemplary embodiment of the present disclosure;

FIG. 6E is a graph illustrating mean cerebral flow rates based on a swept-source optical Doppler tomography system according to an exemplary embodiment of the present disclosure;

FIG. 6F is a graph illustrating vessel diameters based on a swept-source optical Doppler tomography system according to an exemplary embodiment of the present disclosure;

FIG. 9A is a graph of the measured axial point spread functions for various bandwidths according to an exemplary embodiment of the present disclosure;

FIG. 9B is a graph illustrating a comparison between the axial resolution under various fractional bandwidths according to an exemplary embodiment of the present disclosure;

FIG. 9C is a graph illustrating phase noise for different sub-spectra according to an exemplary embodiment of the present disclosure;

FIG. 9D is a graph illustrating phase noise for different fractional bandwidths according to an exemplary embodiment of the present disclosure;

Figures 1A, 1B:
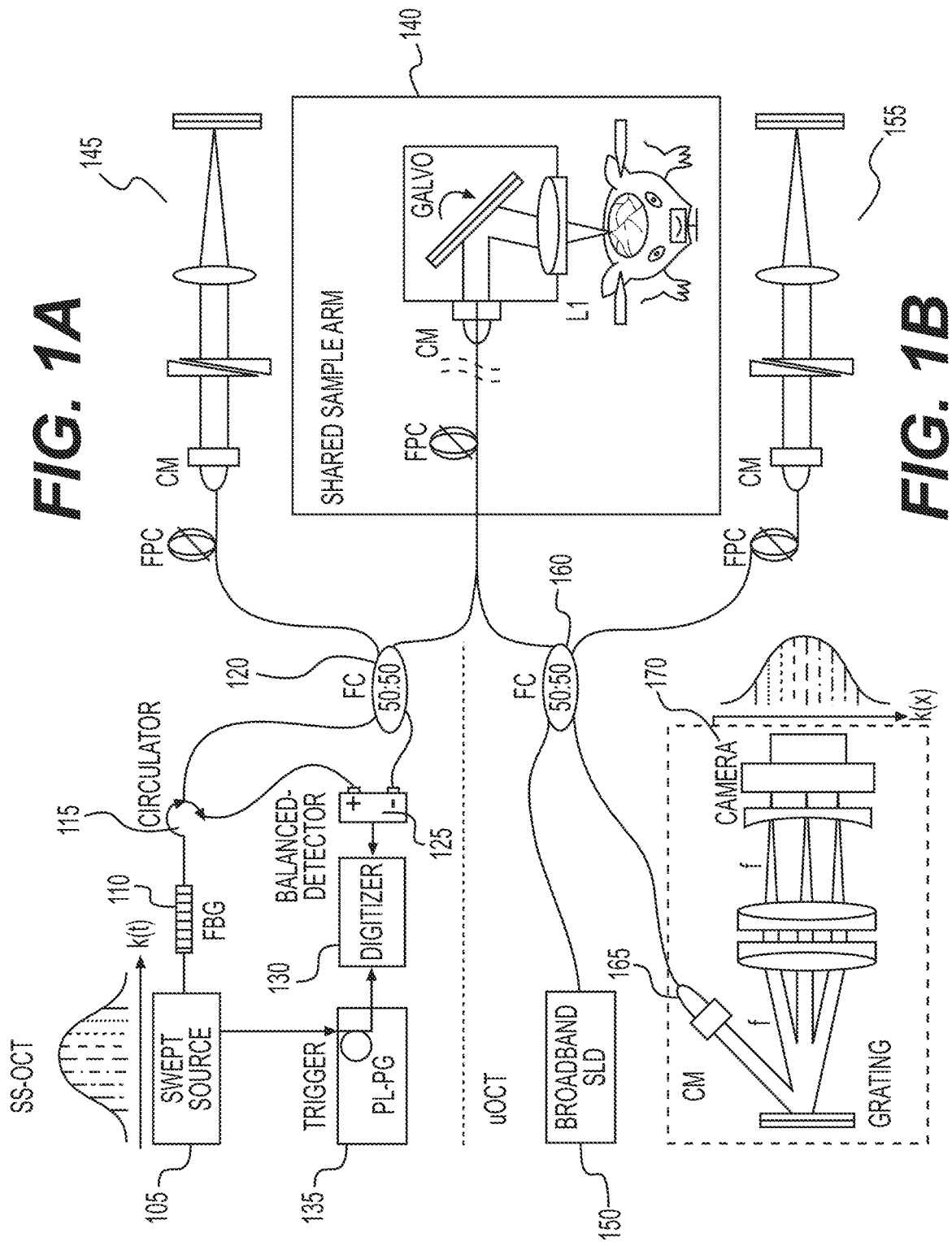
FIG. 1A is an exemplary swept-source optical Doppler tomography system according to an embodiment of the present disclosure.
FIG. 1B is a ultrahigh-resolution spectral-domain optical coherence tomography system.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Known SS-ODT has demonstrated advantages of fast imaging rate and long imaging distance. Limited axial resolution and complex phase noises, however, limits the use of SS-ODT for quantitative capillary blood flow imaging in deep layers of the cortex. The presently described exemplary system, method, and computer-accessible medium can utilize wavelength-division-multiplexing SS-ODT ("WDM-ODT") that can divide a single interferogram from SS-ODT into multiple phase-correlated interferograms, which can enhance the sensitivity for retrieving minute flow-induced Doppler phase shifts. Both flow phantom and in vivo mouse brain imaging studies show that WDM-ODT can significantly suppress background phase noise and detect cerebral capillary blood flow, as well as retinal and epithelial cancer flow imaging, down to vessel size of 5.6 um and flow rate of lower than 100 μm/s. Comparison between WDM-ODT and spectral-domain uODT reveals that WDM-ODT outpaces uODT by extending the depth for deep capillary flow imaging to 1.8 mm below the surface of mouse cortex.

Exemplary Imaging System Setup

FIG. 1A illustrates an embodiment of a modified SS-OCT system. The system includes a 200 kHz VCSEL (Thorlabs, Newton, N.J.) at 1310 nm with a −3 dB wavelength-tuning range of 76 nm. The full spectrum bandwidth of the SS-OCT system corresponds to an axial resolution of 7.20 μm in the mouse cerebral cortex (e.g., gray matter, n=1.38). (See, e.g., Reference 25). A fiber optic Bragg grating ("FBG") filter 110 with the central wavelength of $\lambda_0$=1270.4 nm, reflectivity of 99.9% and spectral bandwidth of $\Delta\lambda$=0.4 nm (OE Land, Quebec, Canada) was inserted between the swept light source 105 and the interferometer (INT-COM-1300 SP4, Thorlabs, Newton, N.J.) for trigger calibration. (See, e.g., Reference 14). Temporally dispersed light fields are launched into a circulator 115 and then split into the sample arm 140 and the reference arm 145 by a 50/50 fiber optic coupler ("FC") 120. The interferogram from the reference arm and the sample arm are detected by a pair of balanced photo detectors 125 (e.g., DC approximately 350 MHz, Thorlabs, Newton, N.J.) and digitized using digitizer 130 (e.g., a 12 bit, 1.8 GS/s data acquisition card, such as ATS9360; AlazarTech, Quebec, Canada), which was externally triggered by a k-clock generated from a delayed Mach-Zehnder interferometer. A high-precision digital pulse generator 135 (DG645; SRS, Sunnyvale, Calif.) is connected to the laser trigger signal to selectively trigger the data acquisition for each A-scan at a designated imaging rate (e.g., at 10 kHz A-scan rate, the pulse generator can trigger the data acquisition every 20 laser sweeps). Sequential A-scans were stored in the workstation (not shown) for two-dimensional ("2D") and three-dimensional ("3D") Doppler flow image reconstruction. In parallel, a camera-based spectral-domain uOCT (see, e.g., FIG. 1B) was incorporated for comparison.

Figure 7A:
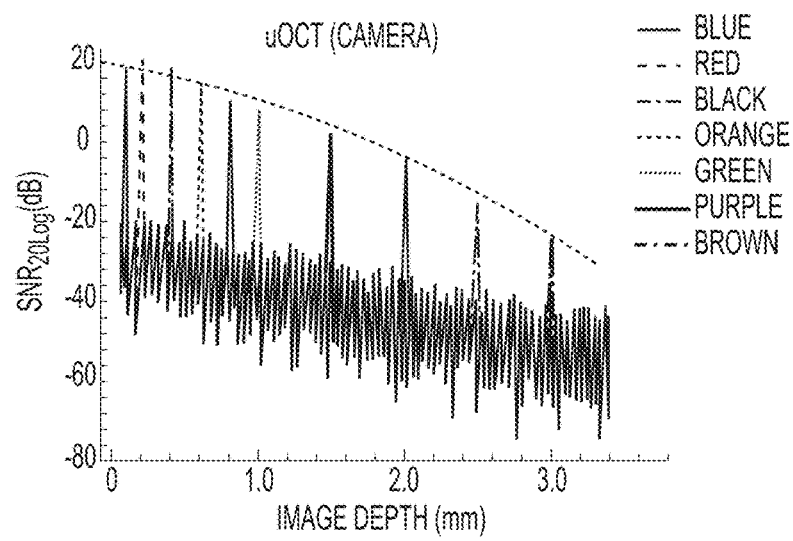
FIG. 7A is a graph illustrating sensitivity roll off for a high resolution optical Doppler tomography system according to an exemplary embodiment of the present disclosure.
Figure 7B:
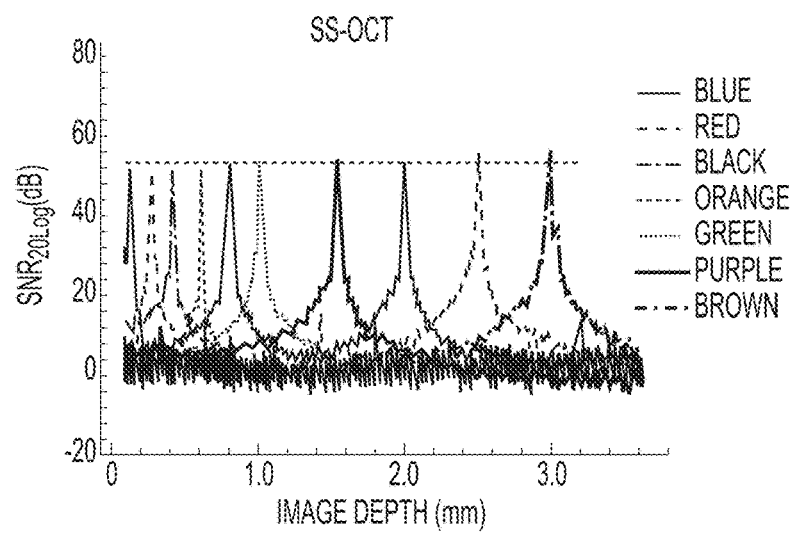
FIG. 7B is a graph illustrating sensitivity roll off for a swept-source optical Doppler tomography system according to an exemplary embodiment of the present disclosure.
Figure 7C:
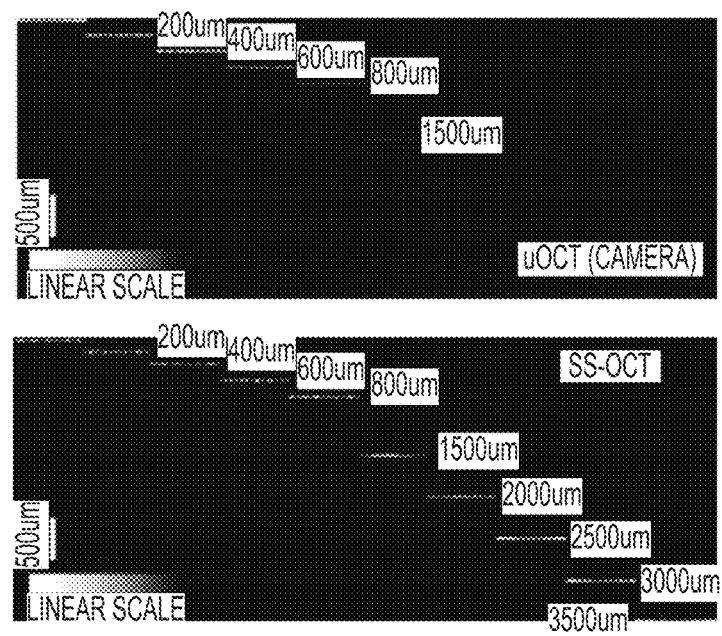
FIG. 7C is a set of intensity images for a high resolution optical Doppler tomography system and a swept-source optical Doppler tomography system according to an exemplary embodiment of the present disclosure.

As shown in FIG. 1B, a broadband superluminescent diode ("SLED") light source 150 (LS2000C; Thorlabs, New Jersey) provides illumination with the central wavelength at 1310 nm and 3 dB spectral bandwidth of 220 nm, which corresponds to an axial resolution of 2.49 µm in the mouse cerebral cortex (e.g., gray matter, n=1.38). (See, e.g., Reference 25). The light field is substantially equally split between the 2 arms in the fiber optic Michelson interferometer (e.g., sample arm 140 and reference arm 155), and the back reflected/scattered light fields are recombined, through FC 160, in the detection fiber 165, spectrally dispersed by a custom high-precision spectrometer and detected by a line-array InGaAs camera 170 (e.g., 2048×1 pixels, up to 147 k lines/s, GL2048; Sensors Unlimited). To ensure an accurate comparison between the SS-OCT and the uOCT for capillary blood flow imaging, these two systems were configured to share the same sample arm 140 (e.g., objective: NA=0.33/f=18 mm, beam size=4.5 mm), which provided the identical scanning field of view and transverse resolution of approximately 5 m. The sensitivity roll-offs of the two systems were characterized by imaging a static mirror at different image depths ($\Delta_z$) with the optical power in sample arm 140 attenuated to approximately 1 mW. The results are shown in FIG. 7A, which illustrates that the system sensitivity of uOCT degraded from 52.26 dB at $\Delta_z$=200 µm to 30.22 dB at $\Delta_z$=3 mm. In comparison, the sensitivity of SS-OCT (e.g., FIG. 7B) maintained unchanged (e.g., approximately 54.9 dB) for $\Delta_z$=200 µm to 3 mm. FIG. 7C is a set of intensity images for the uODT system and the WDM-ODT system.

Exemplary Wavelength-Division-Multiplexing ODT

If the SS-OCT is assumed to be noise-free, the spectral interferometric signal for a cross-sectional B-scan (e.g., FIG. 2A) after subtraction of the background and the autocorrelation term can be written as, for example:

$$i(k, x) = \frac{P}{4} S(k) \sqrt{R_R R_S} \cos(2nkz), \, k \in \Delta k, \quad (1)$$

(see, e.g., Reference 26) where S(k) can be the power spectrum of the swept source, k=2λlλ can be the wavenumber, $R_R$ can be the amplitude of optic field reflected from the reference arm, $R_s$ can be the amplitude of optic field backscattered from the image depth z from the zero optical path difference, and n can be the refractive index of the imaged specimen (e.g., approximately 1.4 for most biological tissue). For conventional ODT, an inverse fast Fourier transform ("FFT") can be applied to the full spectrum, i(k, x) (e.g., spectral profile 205 shown in FIG. 2B) to reconstruct an OCT A-scan intensity profile I(z) and its phase term ΔØ(z, x). Thus, for example:

$$I(z,x) = \text{FFT}\{i(k,x)\} = A(z,x) \exp[i\phi(z,x)] \quad (2)$$

Under the oversampling assumption that the phase variation induced by tissue heterogeneity between subsequent A-scans can be negligible, a phase subtraction method ("PSM") can then be applied to calculate the relative phase change in Eq. (2) between subsequent A-scans, which can be due to the apparent Doppler flow velocity (e.g., axial velocity) of moving scatterers (e.g., red blood cells)(see, e.g., Reference 27), as given by, for example:

$$\Delta\varphi(z, x_n) = \varphi(z, x_{n+1}) - \varphi(z, x_n) = \tan^{-1}\left[\frac{\text{Im}[\tilde{I}(z, x_{n+1}) \cdot \tilde{I}^*(z, x_n)]}{\text{Re}[\tilde{I}(z, x_{n+1}) \cdot \tilde{I}^*(z, x_n)]}\right] \quad (3)$$

In contrast to conventional PSM that utilizes the full spectrum for OCT and Doppler flow image reconstruction based on Eqs. (2) and (3), the exemplary WDM-ODT procedure can divide the full spectrum into P subspectra using a Hamming window optimized to minimize the nearest side lobes (α=0.54) as shown by the dashed lines 210 shown in FIG. 2B. For each sub spectrum, the bandwidth can be (Δk−δk), therefore the first and the last subspectra are spectrally separated in the frequency domain by δk. Δk can be the full spectrum bandwidth and δk can be the decrease in spectrum bandwidth for each sub spectrum. δk can be a quantity of k bandwidth (Δk) loss due to the division of P. (See e.g., FIG. 2D). δk can be related to a full spectrum Δk, where the total number of points is M in the k domain (see e.g., FIG. 2A) as well as the subdivision of P and the k-shift of subspectra. By shifting the filter across the entire spectrum with a step size of δk/P, the subspectra set was obtained with a certain mismatch in the k domain, as shown by the solid profiles 215 shown in FIG. 2D. Both δk and P are chosen to achieve balance between axial resolution and flow sensitivity, which is described below.

Then, for each sub spectrum p (p=1, 2, . . . , P), the interferogram in Eq. (1) can be rewritten as, for example:

$$i(k, x)_p = \frac{P}{4}[S(k)_p \sqrt{R_R} R_S \cos(2kz)], \quad (4)$$

$$k \in \left[k[0] + \frac{p-1}{P}\delta k, k[0] + \frac{p-P-1}{P}\delta k + \Delta k\right],$$

where k[0] can be the initial wavenumber of the output spectrum. The Doppler phase difference between subsequent A-scans φ(z, $x_n$)$_p$ can be calculated accordingly for each subspectrum (e.g., FIG. 2E), and the final Doppler phase difference in WDM-ODT can be given by averaging φ(z, $x_n$)$_p$ over all P sub-spectra (e.g., FIG. 2F) as, for example:

$$\overline{\Delta\varphi}(z, x_n) = \frac{1}{P}\sum_{p=1}^{P}[\varphi(z, x_{n+1})_p - \varphi(z, x_n)_p] = \frac{1}{P}\sum_{p=1}^{P}\tan^{-1}\left[\frac{\text{Im}[\tilde{I}(z, x_{n+1})_p \cdot \tilde{I}^*(z, x_n)_p]}{\text{Re}[\tilde{I}(z, x_{n+1})_p \cdot \tilde{I}^*(z, x_n)_p]}\right] \quad (5)$$

As shown in Eq. (5) the Doppler phase can be calculated by performing a Fourier transform of all subspectra of all A-scans and multiplying the complex field and the conjugate of the complex field for each subspectra between adjacent A-scans. Additionally, the imaginary part of the product can be divided by its real part, and the ArcTan value can be calculated, to determine the phase difference between adjacent A-scans.

Exemplary Optimization of WDM-ODT for Flow Imaging

Due to the triggering jittering (δt) and the variability in either output or sampled spectrum (σk), the detected interferogram in SS-OCT can be modified from Eq. (1) by adding a small random variable εk=αδt+σk in the k-domain (e.g., to include the real clock fluctuation, for example, sampling trigger jittering, and laser wavelength output fluctuation), as shown in, for example:

$$i(k, x) = \frac{P}{4} S(k)\sqrt{R_R R_s} \cos[2n(k+\varepsilon k)z], k \in \Delta k. \tag{6}$$

In the real case, the sampling clock fluctuation in time (δt) and laser output frequency fluctuation in frequency (σk) can both deviate the real detected signal in optical frequency domain away from the ideal value, as described by k+εk, where k can be the ideal frequency. A small random variable εk=αδt+σk in the k-domain can account for the deviation.

Expanding Eq. (6) yields can provide, for example:

$$i(k, x) = \frac{P}{4} S(k)\sqrt{R_R R_S} [\cos(2nkz)\cos(2n\varepsilon kz) - \sin(2nkz)\sin(2n\varepsilon kz)], \tag{6a}$$
$$k \in \Delta k$$

Since εk→0, for a small image depth z, sin(2nεkz)≈0, and cos(2nkz)cos(2nεkz)≈ cos(2nkz)−4n²z(εk)² cos(2nkz), Eq. (3-7) can be simplified as, for example:

$$i(k, x) = \frac{P}{4}\left[S(k)\sqrt{R_R R_S} \cos(2nkz) + N(k)\right], k \in \Delta k \tag{6b}$$

where N(k) can be an additive white Gaussian noise ("AWGN"), for example, a small modulation to the interferogram induced by a small random variable εk. After inverse Fourier transform, the differential phase change between sequential A-scans can be obtained by PSM.

After applying an inverse Fourier transform, the differential phase change between sequential A-scans can be obtained by PSM. (See, e.g., Reference 24). Thus, for example:

$$\Delta\varphi(z,x)=2nk\cdot\Delta z+2n\alpha(\delta t_{n+1}-\delta t_n)\cdot z+2n(\sigma k_{n+1}-\sigma k_n)\cdot z \tag{7}$$

The first term in Eq. (7) can be the moving scatterer-induced Doppler flow phase change as simulated in FIG. 3A. The second term can be the trigger jitter-induced phase artifact, which can be proportional to the image depth z, as simulated in FIG. 3B, and a can be a coefficient to match the unit difference between the term $(\delta t_{n+1}-\delta t_n)\cdot z$ and the phase difference Δφ. The third term can be scanning/sampling variability-induced phase noise due to the random deviations of acquired wave-numbers between subsequent A-scans, which can be simulated as an additive white Gaussian noise (see, e.g., Reference 24), as shown in FIG. 3C. Thus, the total phase change Δφ(z, x) detected in WDM-ODT can be obtained by adding the contributions from origins described above, as shown in FIG. 3D. With spectral calibration procedures, which can include aligning the interferograms between sequential A-scans (see, e.g., References 14 and 28), the trigger jitter-induced phase artifacts can be compensated to eliminate its contribution to the final flow map. The exemplary WDM-ODT procedure can reduce the contribution of this random phase noise by averaging across all P subspectra, which can be expressed as, for example:

$$\overline{\Delta\phi}(z, x_n) = 2nk\cdot\Delta z + 2n\cdot\frac{1}{P}\sum_{p=1}^{P}[\sigma k_{n+1,p} - \sigma k_{n,p}]. \tag{8}$$

A flow phantom study was performed to determine the proper subspectra numbers P and bandwidths for microvascular flow imaging. A microtube of 250 μm inner diameter was used, which was imbedded at approximately 200 μm deep in agarose to mimic the vessels in brain. Inside the microtube, a 1% intralipid solution was directionally infused with its vertical flow rate controlled by a precise syringe pump at 957 μm/s. And the cross-sectional flow profile was imaged by WDM-ODT at 10 k A-scan rate. FIGS. 3E-3G compare the flow images obtained using conventional PSM, trigger jitter-corrected PSM and WDM-ODT method, respectively, including the representation of the microtube in region 305. As shown in FIGS. 3H-3J, which are enlarged images of microtube region 305, the flow image from the exemplary WDM-ODT procedure (FIG. 3J) effectively reduces the random noise pattern in the flow image compared to the flow maps obtained by conventional PSM (FIG. 3H). Defining the flow image signal-to-noise ratio ("SNR") as the ratio between the mean phase change over the SD of the phase change within the flow area (SNR=$\overline{\Delta\phi}$/SD(φ)), the mean SNRs were measured using different subspectra numbers (see e.g., FIG. 3K where P=2 (element 310), 4 (element 315), 8 (element 320), 16 (element 325)) with different fractional bandwidths (e.g., fractional bandwidth=fractional bandwidth=(e. g., Δk−δk)/Δk, from 80% to 20%)).

As shown in FIG. 3K, the large subspectra number used in WDM-ODT can increase the flow SNR at the cost of computational time. The decrease in fractional bandwidth to introduce certain mismatch between the subspectra increased the flow SNR first, while the further narrowing in the subspectra bandwidth (e.g., <50%) exhibited the decreased flow SNR. The decrease in subspectra bandwidth also includes the axial resolution and sacrifices the spectral power for Doppler detection. Based on the curves in FIG. 3K, a subspectra number P=8 (element 320) and the bandwidth (e.g., Δk−δk)/Δk=60% was chosen for the in vivo cerebral capillary imaging study.

Exemplary Results

Exemplary Quantitative Imaging of Cerebral Capillary Flow By WDM-ODT

To demonstrate the performance, the WDM-ODT procedure for capillary flow imaging, in vivo WDM-ODT images were acquired through a cranial window (e.g., Field of view: 2×1.5 mm²) in the mouse sensorimotor cortex. To detect minute capillary flows, a relatively slow A-scan rate at 6 k was used, which was accomplished by down sampling the 200 kHz trigger from the swept source 105 using a high-precision phase-locked pulse generator ("PL-PG") 135 (FIG. 1).

FIGS. 4A-4F compare the in vivo results of microcirculatory flow network imaged using SS-ODT and processed by PSM and WDM-ODT procedures. FIG. 4A shows the en face maximum intensity projection ("MIP") image reconstructed by PSM, in which pial vessels and larger branch vessels in diameters from 20 µm to 100 µm and flow rates higher than 300 µm/s can be readily detected. However, capillary flows that directly perfuse the brain tissue cannot be resolved due to the high background phase noise, as shown in FIG. 4B, which corresponds to a zoomed in area 405 from FIG. 4A. Comparatively, the microcirculatory flow network obtained by WDM-ODT shows dramatically decreased background phase noise, so that the detailed capillary flow network can more readily be resolved, as shown in FIGS. 4C and 4D, which corresponds to zoomed in area 410 from FIG. 4C. Flow profiles for individual vessels along the line A-A' (element 415) and B-B' (element 420) were plotted in FIG. 4E (e.g., trace 420 for PSM and trace 415 for WDM-ODT) for the same brain region. Flow contrast for individual vessels can be defined as the ratio between the maximum flow rate in the center of a vessel and the first minimum flow value at the vessel boundary. As shown in FIG. 4E, WDM-ODT provides an overall improvement in flow contrast for both low and high flows, reducing the noise floor from around 400 µm/s (e.g., trace 420) to around 100 µm/s (e.g., trace 415) with no compromise of the maximum flow rate in the center of vessels. This noise floor reduction can be beneficial for the capillary flow imaging. By randomly selecting 60 vessels across different vessel diameters, FIG. 4F illustrates that capillary flows with vessel diameters less than 15 µm and flow rates less than 400 µm/s were effectively enhanced by WDM-ODT (plotted as dots 425) compared to PSM (plotted as dots 430). The improvement promoted the identification of capillaries at about 5.8 min SS-ODT, approaching the transverse resolution limit of the OCT scan lens. Statistical analyses show that WDM-ODT (e.g., dots 425) enhanced the flow contrasts by 106.4±14.8%, 96.07±9.1%, and 54.12±9.3% for capillaries (0-15 µm), arterioles/venules (15-30 µm) and pial arteries/veins (30-60 µm) over conventional PSM (e.g., dots 430). Therefore, the exemplary system, method, and computer-accessible medium can significantly improve the sensitivity for microvascular flow imaging, especially for capillary flow imaging.

Exemplary WDM-ODT Vs. Spectral-Domain uODT in Capillary Flow Imaging

Figures 8A, 8B:
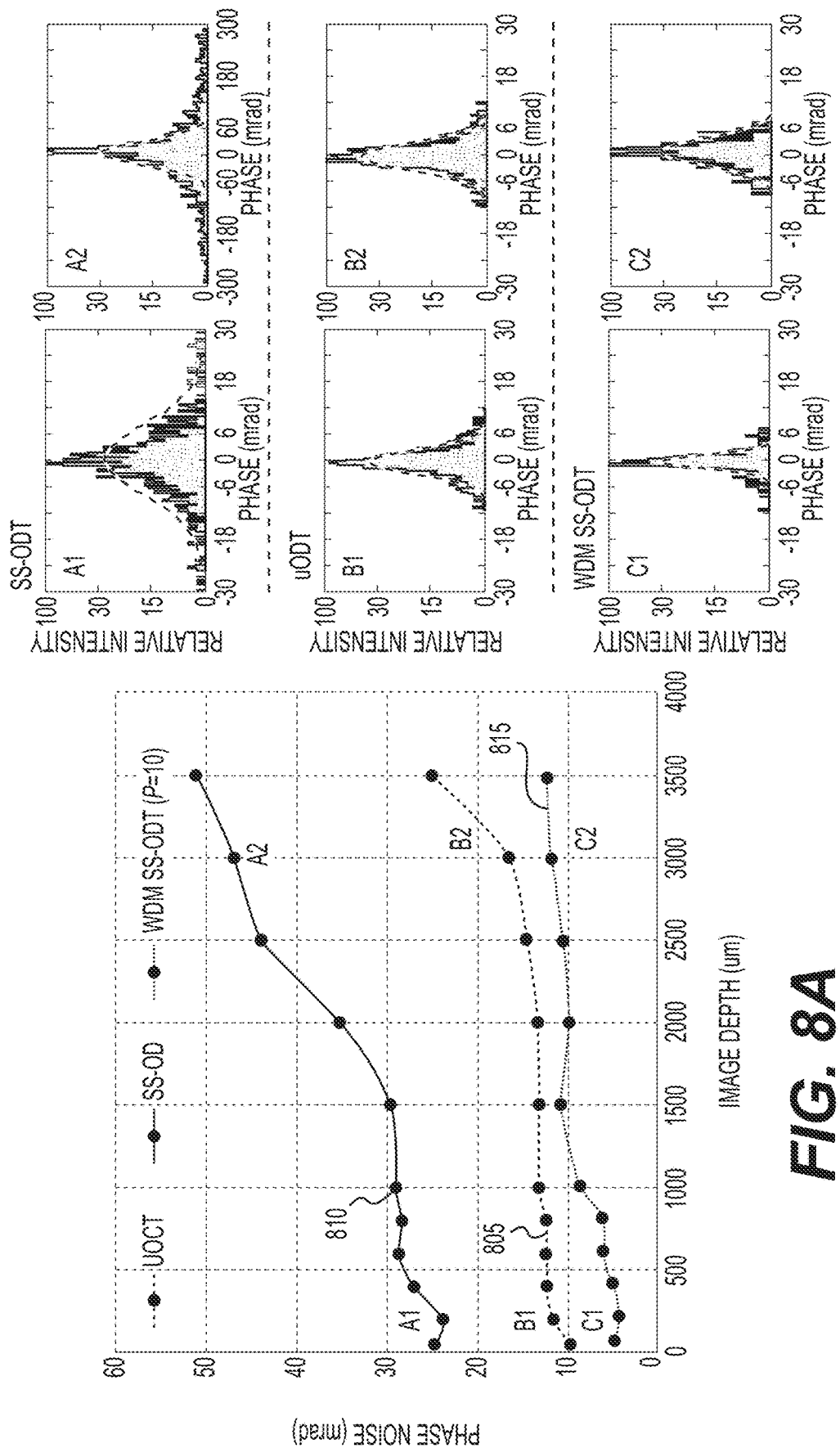
FIG. 8A is a graph illustrating phase noise versus image depth of a high resolution optical Doppler tomography system, a swept-source optical Doppler tomography system, and a wavelength division multiplexing swept-source optical Doppler tomography system according to an exemplary embodiment of the present disclosure.
FIG. 8B is a set of histograms of different phase distributions according to an exemplary embodiment of the present disclosure.

The phase stabilities for a SS-ODT system, an SS-ODM system with the present WDM methodology, and a uODT system at different image depths is shown in FIGS. 8A and 8B. The phase noise level of the camera-based uODT (trace 805) was 13.4 mrad at $\Delta z=200$ µm and maintained at approximately 15 mrad to $\Delta z=2.5$ mm. Then, it started to increase to 16.6 mrad at 3 mm and to 25.1 mrad at 3.5 mm, which may be due to the decrease of the system SNR. As expected, SS-ODT (trace 810) exhibited an overall higher phase noise level (e.g., 23.87 mrad at 200 µm (point A1) and 46.87 mrad at 3 mm (point A2)); however, applying WDM (trace 815) decreased the phase noise to approximately 5.4 mrad at 200 µm (point C1) and remained approximately 10 mrad for $\Delta_z=1\text{-}3$ mm (point C2) (e.g., as low as that of uODT). Thus, WDM-ODT provided sufficient SNR for cerebral capillary flow imaging as had been reported with uODT.

Figure 5H:
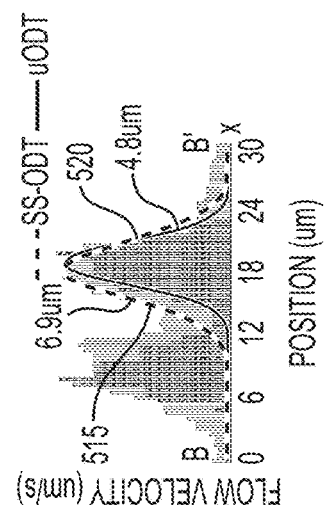
FIG. 5H is a side view image of the capillary network shown in FIG. 5G according to an exemplary embodiment of the present disclosure.

To further examine the utility of WDM-ODT for capillary flow imaging, mouse in vivo cerebral flow imaging with WDM-ODT and uODT was performed that shared the same sample optics (e.g., with the focal plane placed at approximately 400 µm below the cranial surface). Flow images acquired by WDM-ODT and uODT were reconstructed with WDM-ODT and PSM, respectively. FIGS. 5A and 5B plot the power spectra of the ultra-broadband SLED and the VCSEL swept source, respectively. FIGS. 5C and 5D show the en face MIP images of the quantitative cerebral microvascular flow network acquired by uODT and WDM-ODT. Despite a relatively low axial resolution, the WDM-ODT system was able to provide high capillary flow imaging sensitivity comparable to the capillary flow imaging obtained using uODT. By further examining the zoom-in images in FIGS. 5E and 5G (which correspond to areas 505 and 510 from FIGS. 5C and 5D, respectively), subtle differences between these imaging methods were noticed. For instance, because of the higher axial resolution in uODT system, capillary flows can be thinner and their edges can be sharper. This can be because the higher axial resolution in uODT can lead to a smaller speckle size (e.g., including dynamic speckles) even with the same transverse resolution as in the WDM-ODT system, which results in a better resolution of capillaries in Doppler flow imaging. On the other hand, more capillary flows can be present in the en face MIP flow image obtained by WDM-ODT. This increase in capillary density can be based on the slow SNR decay of the WDM-ODT system vs. the imaging depth; thus more microflows in the deeper cortex can be visualized. This difference is more evident in the cross-sectional MIP images shown in FIGS. 5F and 5H. Both systems were able to resolve the capillary flows at the cortical depths of 500 µm (e.g., line 525). Below 500 µm, flow signals in the uODT system decayed rapidly as the image depth increased and showed the noise floor increase. On the contrary, capillary flows continued to be well resolved in the WDM-ODT up to 800 µm (e.g., line 530) and the increase of background noise was minor until 1.1 mm. Thus, the WDM-ODT system showed obvious advantages for the cerebral capillary flow imaging located in the deep cortex.

Figure 5J:
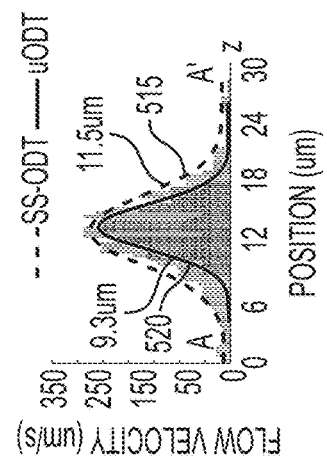
FIGS. 5I and 5J are graphs illustrating position versus flow velocity for the images illustrated in FIGS. 5G and 5H, respectively.
Figure 5G:
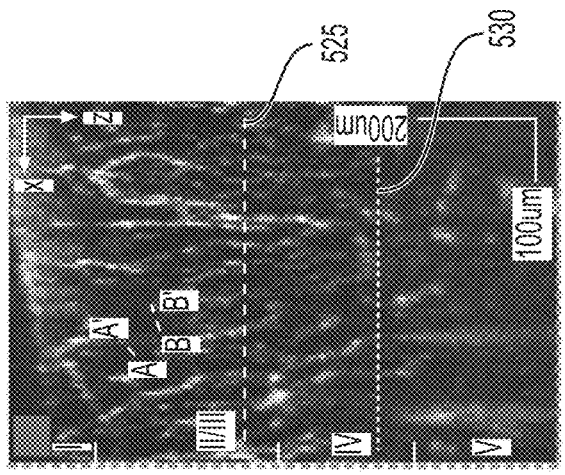
FIG. 5G is a zoomed in view of the image from FIG. 5D according to an exemplary embodiment of the present disclosure.
Figure 5I:
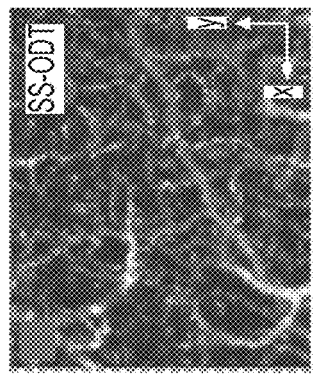

Since the uODT and the WDM-ODT systems show different resolutions for the same vessels, flow profiles (e.g., A-A', B-B') of the same capillaries imaged were selected from the cross-sectional MIP images (e.g., FIGS. 5F and 5H) for a quantitative comparison. FIGS. 5I and 5J show that the flow profiles of A-A' and B-B' were 11.5 and 6.9 µm, respectively (e.g., curves 515), using WDM-ODT, which were larger than 9.3 and 4.8 µm by uODT (e.g., curves 520). This broadening of the capillary flow profiles may be caused by the lower axial resolution in WDM-ODT system. However, the discrepancy regarding the capillary profiles between the uODT and the WDM-ODT can be only 2-3 µm, which may not substantially affect the major cerebral vessel network imaging. Thus, despite limited wavelength-tuning ranges of current swept-source technologies, WDM-ODT can provide comparable capillary flow sensitivity and image quality compared to the uODT system.

FIGS. 6A and 6B show a 3D rending of cerebral blood flow network in a mouse sensorimotor cortex imaged by uODT (e.g., FIG. 6A) and SS-ODT using WDM-ODT (e.g., FIG. 6B). The SS-ODT enhanced using the exemplary WDM-ODT procedure was able to reach the vessel network up to 1.6 mm deep in the cortex compared to 1.2 mm by uODT. This improvement shows that WDM-ODT can be used to image the microcirculatory flow network in mouse cortex as deep as the results that have been reported by multiphoton microscopy (See, e.g., References 29 and 30). The increase of flow image depth in WDM-ODT system permits a better visualization of the CBFv distribution and vascular hierarchy in the mouse cortex. For example, the sectional 3D flow image stacks in FIG. 6C show the transition of the cerebral vascular network from large horizontal pial flows almost parallel to the cortical surface (z: 0-400

μm), to penetrating arterial/venous flows and spreading arterioles/venules flows (z: 400-800 μm), and to the predominant capillary flow networks located at the deep cortex (z: 800-1200 μm). The ending terminals of penetrating arterioles and venules can be observed between 1.2 and 1.6 mm where the capillary flow density decreases. WDM-ODT supports better microvascular imaging over uODT in the deep cortices, for example, layer 5 and layer 6 of the sensorimotor cortex, which can play an active role in brain response to sensory stimulations. Based on the 3D cerebral blood flow network from WDM-ODT, the 3D microvascular skeleton and corresponding vessel diameters were extracted using a vessel segmentation toolbox (Amira 5.4.3; FEI Visualization Sciences Group, Hillsboro, Oreg.). As shown in FIG. 6D, the vascular skeleton can be encoded and delineated proportional to the vessel diameters, ranging from capillaries less than 10 μm to large vessels up to 50 μm. This topological information can be further correlated with the 3D CBFv map in FIG. 6B to compare the mean blood flow velocity and vessel diameters at different cortical depths. As shown in FIGS. 6E and 6F, the mean CBFv decreases as the vessel diameter decreases from the cortical surface to the deep brain regions. The lowest CBFv rates and the minimum vessel diameters can be observed around 700 μm beneath the cortical surface, corresponding to the highest capillary density at this cortical depth in the mouse sensorimotor cortex. The measurement of vessel diameters outside the focal plane can be inaccurate due to the degradation of transverse resolution; however, the overestimation can be limited to approximately 10 μm even at the 1.2 mm imaging depth based on the simulation.

Ultrasensitive phase imaging, especially the cerebral capillary flow imaging, can be challenging for SS-ODT due to the inherent phase instability and complex phase noise origins. While the trigger jitter-induced spectral shifts have been widely discussed and addressed using different methods (see, e.g., References 23 and 28), the scanning variability-associated random phase deviations may not be well resolved, which can affect quantitative capillary flow imaging for SS-ODT. Thus, the exemplary system, method, and computer-accessible medium can be used to eliminate the scanning variability-induced random phase noise by dividing a single interferogram from SS-ODT into multiple phase-correlated interferograms and retrieving the Doppler phase change via spectral multiplexing.

The exemplary system, method, and computer-accessible medium can utilize an optimized combination of the subspectra number and the fractional bandwidth to achieve a balance between the flow SNR, computational cost, and the axial resolution. As the decrease in fractional bandwidth can reduce the axial resolution (see, e.g., Reference 26), the axial resolution or the axial PSF was measured using different fractional bandwidths from 100% to 10% at a fixed subspectra number (P=10). FIGS. 9A-9D plot the profiles of axial PSFs for various fractional bandwidths. For example, FIG. 9A shows fractional bandwidths of f.b.=10% (element 905), f.b.=20% (element 910), f.b.=30% (element 915), f.b.=40% (element 920), f.b.=50% (element 925), f.b.=60% (element 930), f.b.=70% (element 935), f.b.=80% (element 940), f.b.=90% (element 945), f.b.=100% (element 950). The measured axial resolution degraded from 8.69 μm in air with 100% bandwidth (e.g., 75.5 nm) to 52.16 μm with only 10% of fractional bandwidth, among which the decrease was dramatic when the fractional bandwidth was reduced to less than approximately 60% (e.g., axial resolution=11.59 μm). This result suggests that degrading of axial resolution for WDM SS-OCT can be less a concern if the fractional bandwidth can be broader than 60% of the full spectrum.

The increase of subspectra numbers and decrease of the fractional bandwidth can improve the flow sensitivity. The phase noise analysis showed that (i) the increase of subspectra numbers decreased the phase noise of SS-ODT from approximately 15 mrad for P=2 to approximately 5 mrad for P=10, after which the improvement reached a plateau and (ii) the reduced fractional bandwidth decreased the phase noise from 18.7 mrad with 100% to 5.3 mrad with approximately 60% of the full spectrum, but further decreasing the fractional bandwidth to 10% can deteriorate the phase noise 31.2 mrad (e.g., FIGS. 8C and 8D). The exemplary phantom study shows that the flow SNR improvement can be associated with an increase of the subspectra numbers at higher computational costs, while the flow SNR can have a local maximum value regarding the fractional bandwidth.

It can be challenging to quantitatively analyze the maximum imaging depth of microvascular imaging in mouse brain using SS-ODT since the achievable imaging depth can be confounded by the effects of tissue scattering, SNR roll-off and the depth of field of the imaging beams. The analysis of sensitivity roll-off and phase noise levels at different image depths (e.g., FIGS. 7A, 7B, 8A and 8B) shows that the present WDM procedure minimizes the phase noise of SS-ODT to a comparable low level as that of uOCT (e.g., 13 mrad at 2.5 mm uOCT, 10.71 mrad at 2.5 mm for WDM-ODT). Due to slow SNR roll-off, WDM-ODT can have the advantage over uODT for imaging the capillary flow networks in deep cortex (e.g., less than 1.6 mm). Non-diffractive beams can also be combined with the exemplary WDM-ODT system to achieve better flow imaging depths and more accurate vascular network quantifications. The exemplary system, method, and computer-accessible medium can also be used in ophthalmology, and other area, including intraoperative human brain imaging using OCT to help identify tumor margins located at 500 to 1.5 mm beneath the cortical surface. (See, e.g., Reference 35).

To provide higher sensitivity Doppler flow detection (e.g., cerebral blood flow velocity) at a fast frame rate, rather than perform phase subtraction between adjacent A-lines of a single beam (e.g., a single probing ODT laser beam), a dual-beam system can be employed in which phases between dual probing beams that are spatially separated are subtracted. The dual=beam system can utilize the second (e.g., spare or unused) output channel of a swept source and the second A/D channel (e.g., unused or spare) of ultrafast data acquisition ("DAQ") card. Fiber polarization controllers can be used to maximize the p-, s-waves in the two sample beams to be combined by a polarization beam splitter into a colinear beam, which can then be split by a Wollaston prism into two beams with a small angle θ (e.g., 1o), resulting a lateral shift Δx≈f×tan θ over the tissue surface to be imaged. The separation Δx can be adjusted by the combination of focal length ("f") and θ (e.g., which can be determined by the length of birefringent crystal) cut angle and Δn.

Figure 10A:
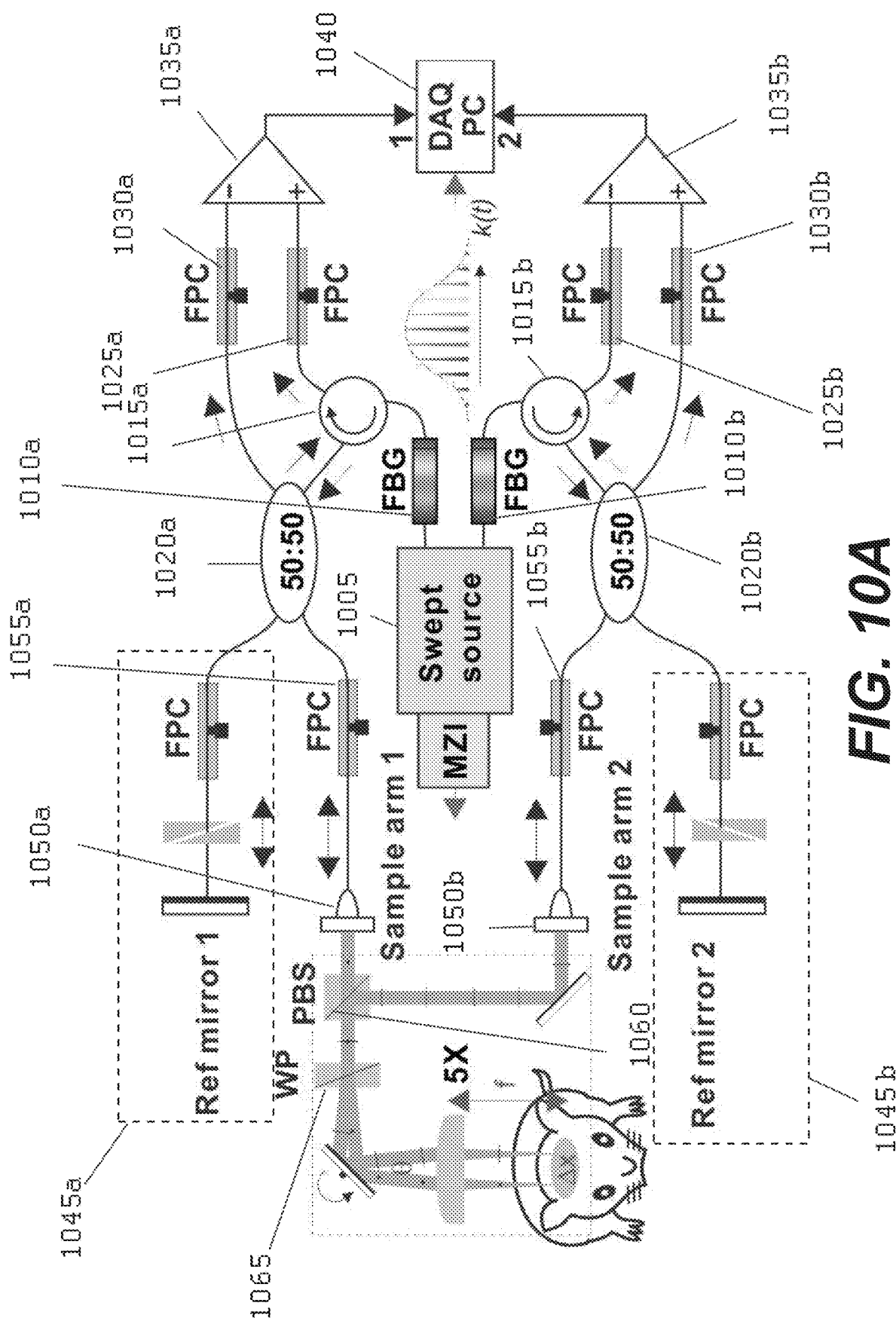
FIG. 10A is a simplified block diagram of an exemplary dual-beam ss-ODT system according to the present disclosure.

FIG. 10A provides a simplified schematic diagram of an exemplary dual beam SS-ODT system according to an exemplary embodiment of the present disclosure. The system includes a common swept source 1005 which can be coupled to FBGs 1010a and 1010b in each of the two respective beam channels. Each of FBGs 101a and 1010b can be coupled to respective circulators 1015a and 1015b, which in turn can be coupled to a 50/50 FC on a first port, and a fiber polarization controller ("FPC") 1025 on a second port of the respective circulator (e.g., circulators 1015a or

1015*b*). A return port on FC 1020*a* can be coupled through a second FPC 1030 to a differential amplifier 1035*a*. The differential amplifier 1035*a* can also be coupled to the swept source 1005 via the circulator 101*a* and FPC 1025*a*. The output of differential amplified 1035*a* can be coupled to a digitizer/data acquisition module 1040 and to a processor (e.g., as described below in FIG. 12).

Each channel in the dual-beam SS-ODT of FIG. 10A can further include a reference arms 1045*a* and 1045*b*, respectively, coupled to the FCs 1020*a* and 1020*b*, a sample arm, including collimators 1050*a* and 1050*b*, and FPCs 1055*a* and 1055*b*, also coupled to FCs 1020*a* and 1020*b*. A polarization beam splitter PBS 1060 can combine the sample output beams from the respective sample arms into a collinear beam that can be provided to a Wollaston prism ("WP") 1065. The WP 1065 can split the collinear beam with an angle θ (e.g. 1°), introducing a lateral shift between the two beams. The resulting lateral shift between the two beams, Δx, can be approximately equal to f×tan(θ).

The two retroreflected beams can be combined with their own reference beams to generate two sets of OCT images. Instead of using PSM between two adjacent A-scans to extract Doppler flow, which requires sufficient time to detect capillary flow (e.g. 5K fps), PSM is applied to extract Doppler flow between two sample beams which are temporally delay by Δx/v where v can be the scanning speed of the mirror G. With proper separation, such as Δx=300 μm and f=18 mm, equivalent 5K fps capillary flow sensitivity can be achieved at a full 200 kHz ss-ODT rate, or a forty times increase in acquisition speed resulting from the dual beam approach.

Figure 10B:
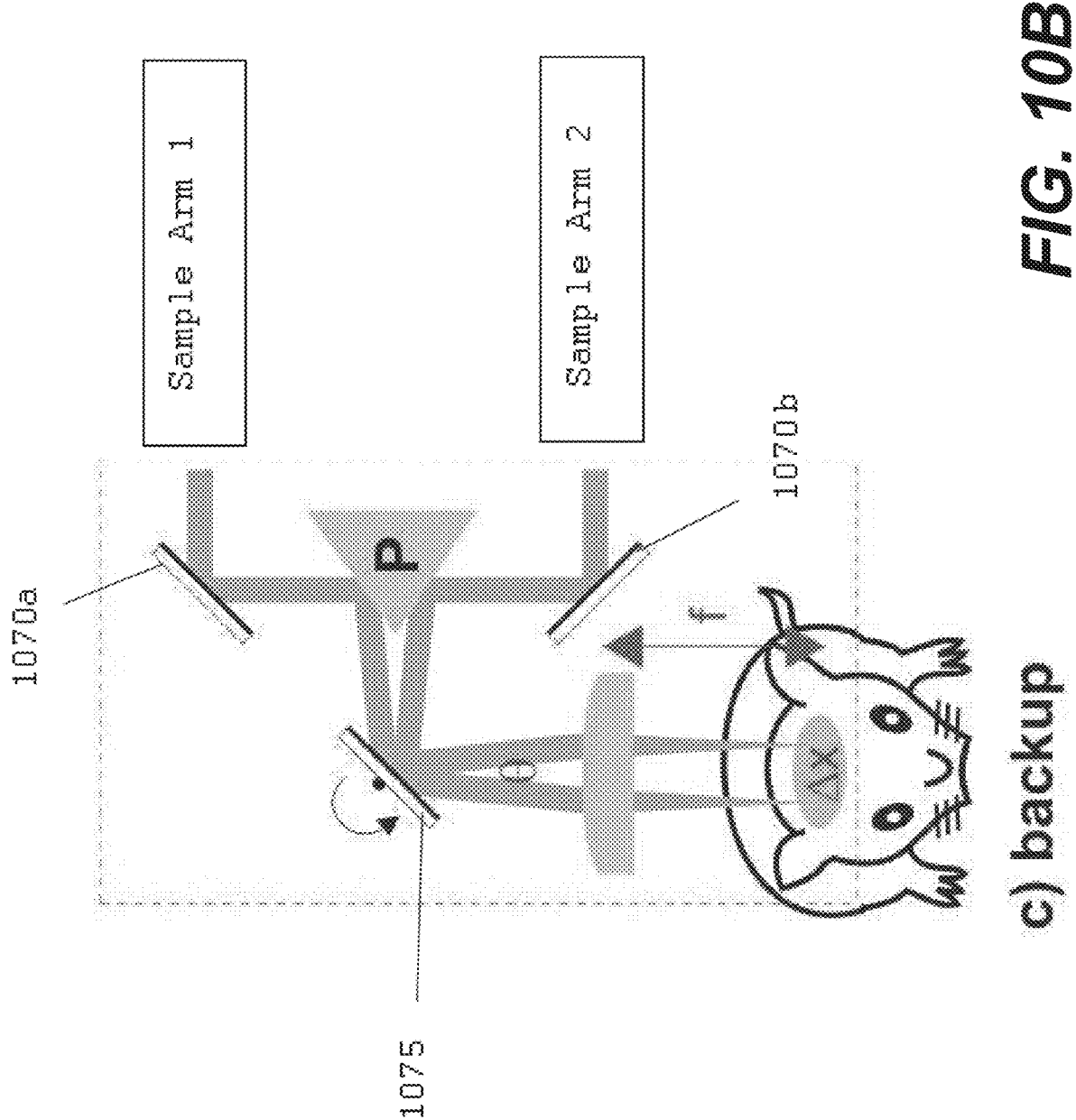
FIG. 10B is a simplified block diagram of a further exemplary dual-beam ss-ODT system according to the present disclosure.

FIG. 10B provides an alternative embodiment for generating the desired lateral shift in the two beams. Rather than use the polarizing beam splitter 1060 and WP 1065 as described in FIG. 10A, the exemplary embodiment in FIG. 10B can use 90° mirrors 1070*a* and 1070*b* and a reflective prism 1075 to create the shift, Δx.

FIGS. 11A-11D are flow diagrams of methods 1100, 1120, 1140, and 1160 for generating an image of a 3D anatomical flow map according to an exemplary embodiment of the present disclosure.

Figure 11A:
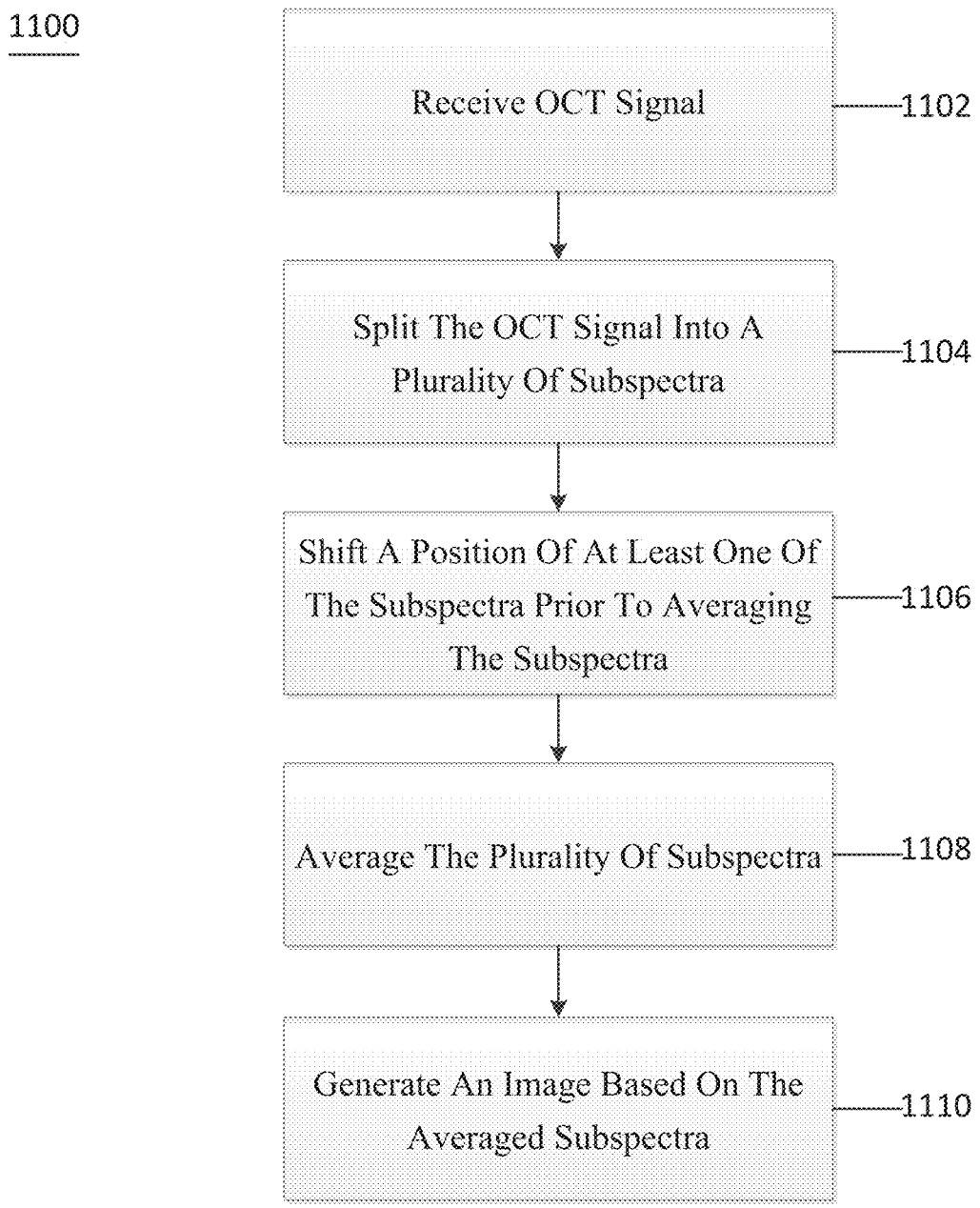
FIGS. 11A-11D are flow diagrams of methods for generating an image of a 3D anatomical flow map according to exemplary embodiments of the present disclosure.

For example, as shown in method 1100 of FIG. 11A, at procedure 1102, an OCT signal can be received. At procedure 1104, the OCT signal can be split into a plurality of subspectra. At procedure 1106, a position of at least one of the subspectra can be shifted, and the plurality of subspectra can be averaged at procedure 1108. At procedure 1110, an image of a 3D anatomical flow map can be generated based on the averaged subspectra.

Figure 11B:
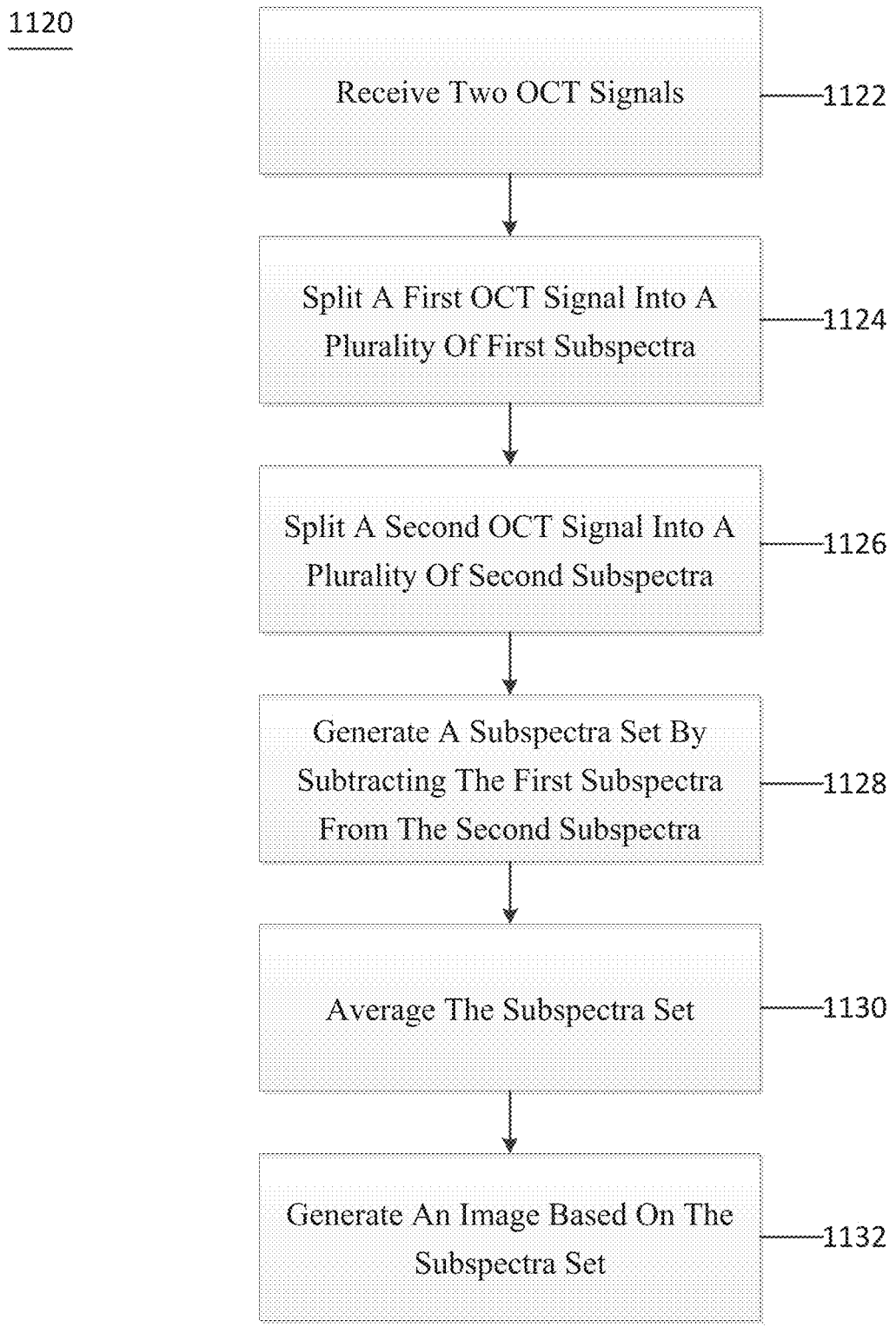

As shown in method 1120 of FIG. 11B, at procedure 1122, two OCT signals can be received. At procedure 1124, a first OCT signal can be split into a plurality of first subspectra and at procedure 1126, a second OCT can be split into a plurality of second subspectra. At procedure 1128, a subspectra set can be generated by subtracting the first subspectra from the second subspectra. At procedure 1130, the subspectra set can be averaged. At procedure 1132, an image of a 3D anatomical flow map can be generated based on the subspectra set (e.g., the averaged subspectra set).

Figure 11C:
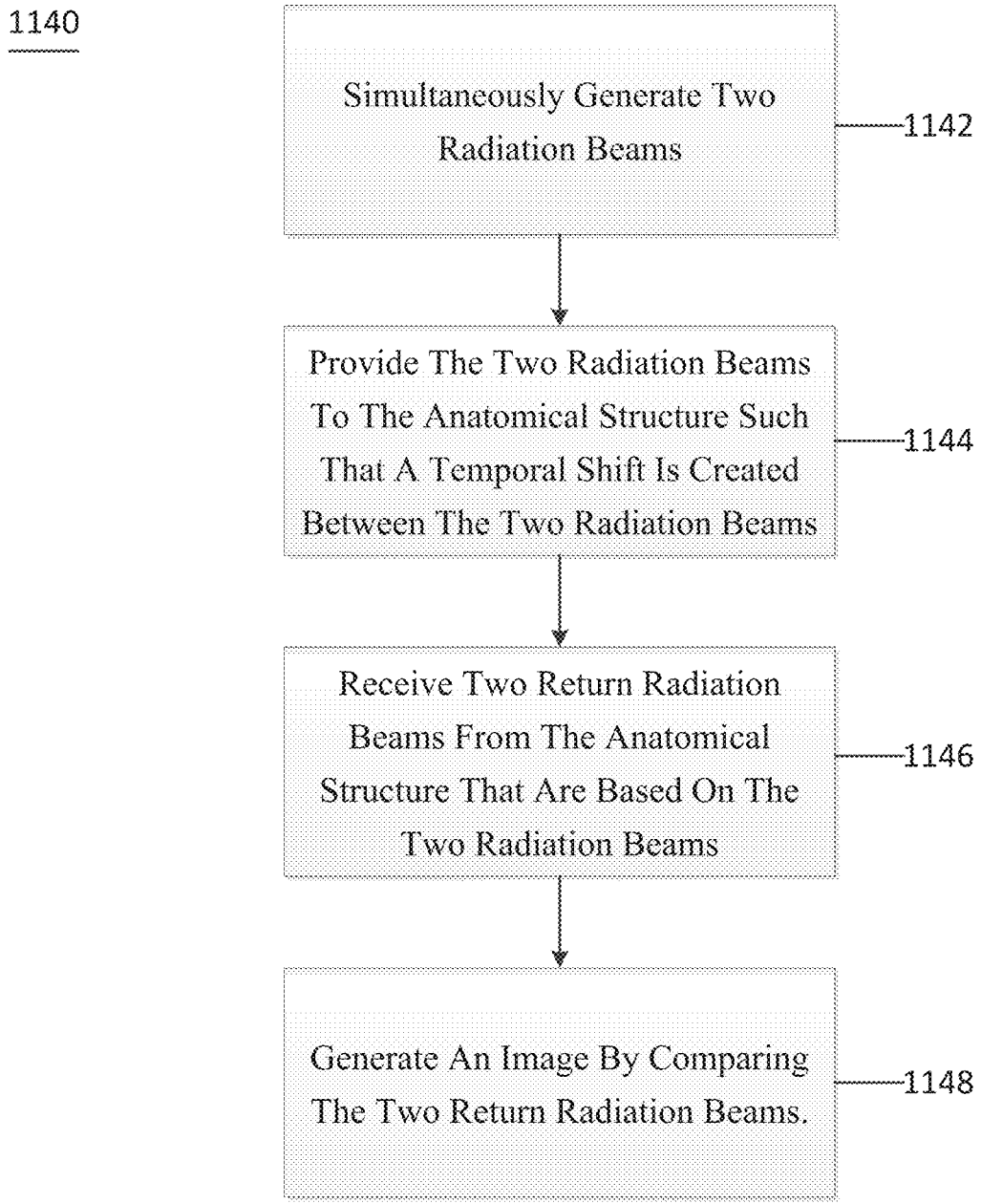

As shown in method 1140 of FIG. 11C, at procedure 1142, two radiation beams can be simultaneously generated. At procedure 1144, the two radiation beams can be provided to an anatomical structure such that a temporal shift is created between the two radiation beams. At procedure 1146, two return radiation beams can be received from the anatomical structure which can be based on the two radiation beams. At procedure 1148, an image of a 3D anatomical flow map can be generated by comparing the two return radiation beams.

Figure 11D:
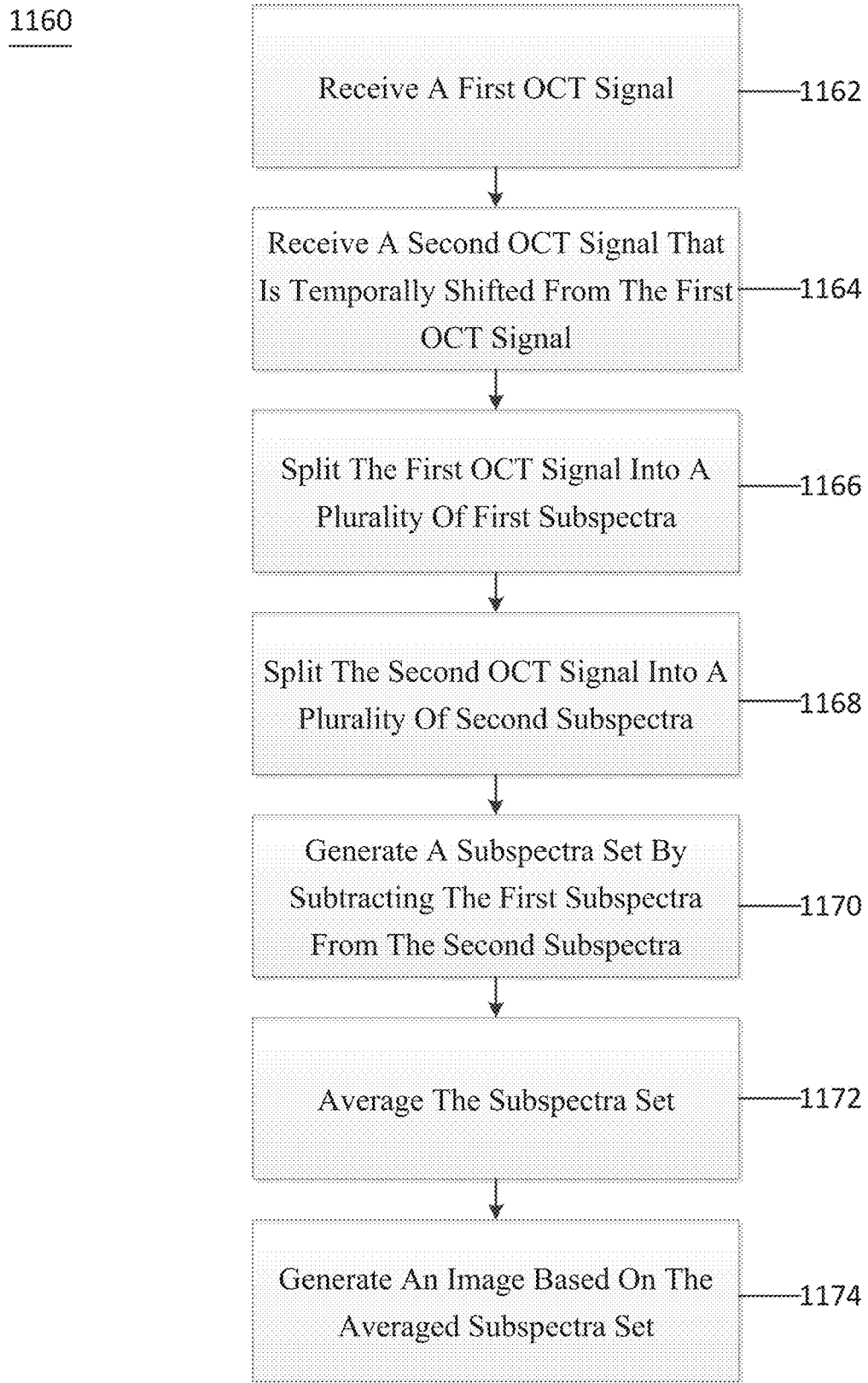

As shown in method 1160 of FIG. 11D, at procedure 1162, a first OCT signal can be received. At procedure 1164, a second OCT signal can be received that is temporally shifted from the first PCT signal. At procedure 1166, the first OCT signal can be split into a plurality of first subspectra. At procedure 1168, the second OCT signal can be split into a plurality of second subspectra. At procedure 1170, a subspectra set can be generated by subtracting the first subspectra from the second subspectra. At procedure 1172, an averaged subspectra set can be generated. At procedure 1174, an image of a 3D anatomical flow map can be generated based on the averaged subspectra set.

Figure 12:
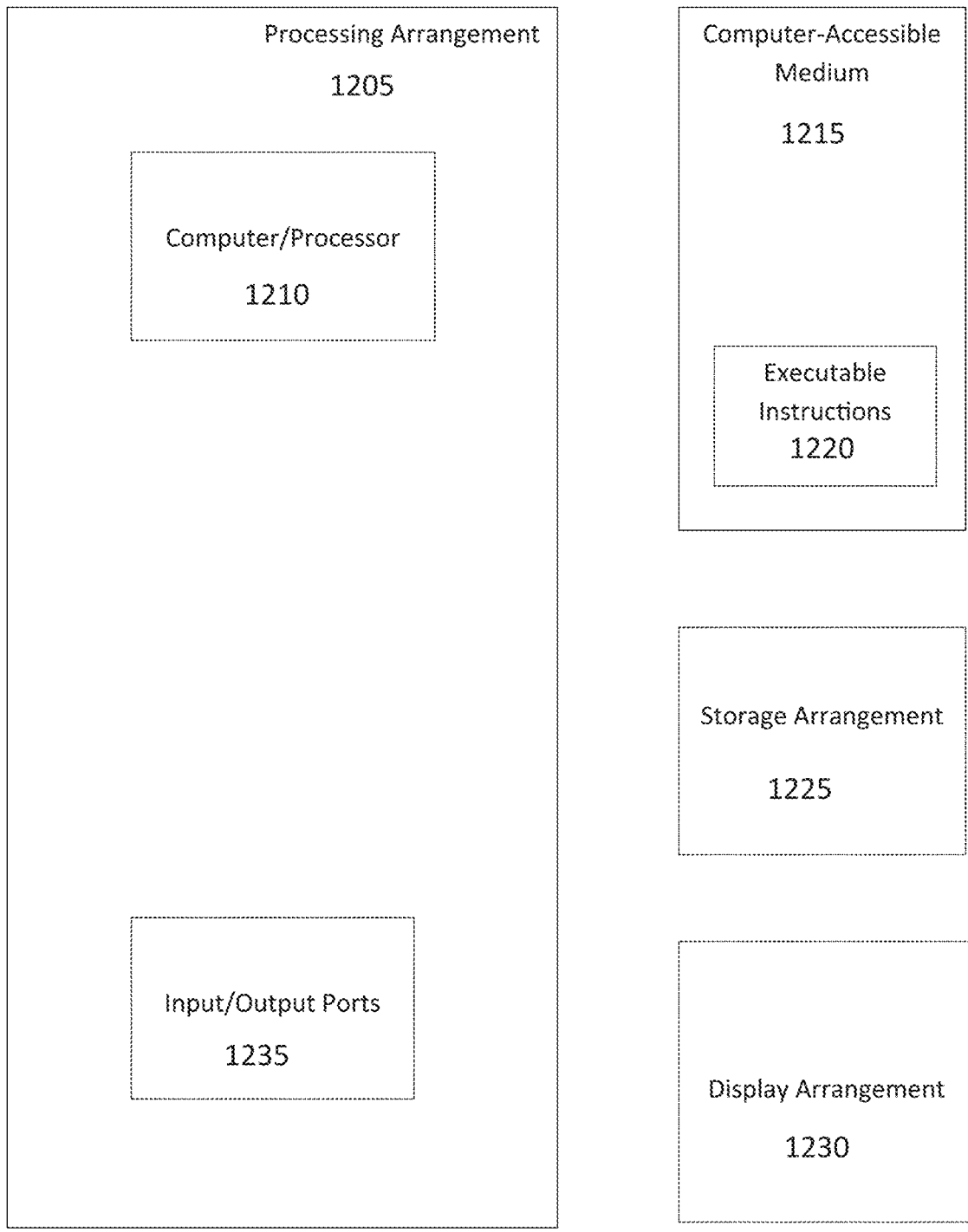
FIG. 12 is an illustration of an exemplary block diagram of an exemplary system in accordance with certain exemplary embodiments of the present disclosure.

FIG. 12 shows a block diagram of an exemplary embodiment of a processing system according to the present disclosure, which can be used to perform method 200 described above. For example, exemplary procedures in accordance with the present disclosure described herein (e.g., methods 1100, 1120, 1140, and 1160) can be performed by a processing arrangement and/or a computing arrangement (e.g., computer hardware arrangement) 1205. Such processing/computing arrangement 1205 can be, for example entirely or a part of, or include, but not limited to, a computer/processor (or a graphics processing unit) 1210 that can include, for example one or more microprocessors, and use instructions stored on a computer-accessible medium (e.g., RAM, ROM, hard drive, or other storage device).

As shown in FIG. 12, for example a computer-accessible medium 1215 (e.g., as described herein above, a storage device such as a hard disk, a high-speed hard disk (magnetic or solid state), floppy disk, memory stick, CD-ROM, RAM, ROM, etc., or a collection thereof), which can include methods 1100, 1120, 1140, and 1160 stored thereon, can be provided (e.g., in communication with the processing arrangement 1205). The computer-accessible medium 1215 can contain executable instructions 1220 thereon to execute methods 1100, 1120, 1140, and 1160. In addition or alternatively, a storage arrangement 1225 can be provided separately from the computer-accessible medium 1215, which can provide the instructions to the processing arrangement 1205 so as to configure the processing arrangement to execute certain exemplary procedures, processes, and methods (e.g., methods 1100, 1120, 1140, and 1160), as described herein above, for example. Exemplary procedures can include, receiving an OCT signal, splitting the OCT signal into a plurality of subspectra, averaging the plurality of subspectra, and generating an image based on the averaged subspectra.

Further, the exemplary processing arrangement 1205 can be provided with or include an input/output ports 1235, which can include, for example a wired network, a wireless network, the internet, an intranet, a data collection probe, a sensor, etc. As shown in FIG. 12, the exemplary processing arrangement 1205 can be in communication with an exemplary display arrangement 1230, which can display the generated image, and which, according to certain exemplary embodiments of the present disclosure, can be a touch-screen configured for inputting information to the processing arrangement in addition to outputting information from the processing arrangement, for example. For example, display arrangement 1230 can be used to display imaging information to a user (e.g., a doctor), which can provide input to perform a segmenting operating on the imaging information. Further, the exemplary display arrangement 1230 and/or a storage arrangement 1225 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties.

[1] W. Chang, T. Flotte, J. G. Fujimoto, K. Gregory, M. R. Hee, D. Huang, C. P. Lin, C. A. Puliafito, J. S. Schuman, W. G. Stinson, E. A. Swanson, Science 1991, 254, 1178.
[2] B. J. Vakoc, R. M. Lanning, J. A. Tyrrell, T. P. Padera, L. A. Bartlett, T. Stylianopoulos, L. L. Munn, G. J. Tearney, D. Fukumura, R. K. Jain, Nat. Med. 2009, 15, 1219.
[3] U. Baran, R. K. Wang, Neurophotonics 2016, 3, 010902.
[4] A. Al-Mujaini, U. K. Wali, S. Azeem, Oman Med. J. 2013, 28, 86.
[5] C.-L. Chen, R. K. Wang, Biomed. Opt. Express 2017, 8, 1056.
[6] V. J. Srinivasan, H. Radhakrishnan, E. H. Lo, E. T. Mandeville, J. Y. Jiang, S. Barry, A. E. Cable, Biomed. Opt. Express 2012, 3, 612.
[7] V. Yang, M. Gordon, B. Qi, J. Pekar, S. Lo, E. Seng-Yue, A. Mok, B. Wilson, I. Vitkin, Opt. Express 2003, 11, 794.
[8] W. M. Allen, L. Chin, P. Wijesinghe, R. W. Kirk, B. Latham, D. D. Sampson, C. M. Saunders, B. F. Kennedy, Biomed. Opt. Express 2016, 7, 4139.
[9] S. A. Boppart, A. L. Oldenburg, C. Xu, D. L. Marks, J. Biomed. Opt. 2005, 10, 41208.
[10] H. Ren, C. Du, Z. Yuan, K. Park, N. D. Volkow, Y. Pan, Mol. Psychiatry 2012, 17, 1017.
[11] Y. Zhao, Z. Chen, C. Saxer, S. Xiang, J. F. de Boer, J. S. Nelson, Opt. Lett. 2000, 25, 114.
[12] J. You, N. D. Volkow, K. Park, Q. Zhang, K. Clare, C. Du, Y. Pan, JCI Insight 2017, 2, 5.
[13] V. J. Srinivasan, E. T. Mandeville, A. Can, F. Blasi, M. Climov, A. Daneshmand, J. H. Lee, E. Yu, H. Radhakrishnan, E. H. Lo, PLoS One 2013, 8, e71478.
[14] W. Chen, J. You, X. Gu, C. Du, Y. Pan, Sci. Rep. 2016, 6, 38786.
[15] W. Chen, K. Park, N. Volkow, Y. Pan, C. Du, IEEE J. Sel. Top. Quant. Electron. 2016, 22, 1.
[16] M. Choma, M. Sarunic, C. Yang, J. Izatt, Opt. Express 2003, 11, 2183.
[17] I. Grulkowski, J. J. Liu, B. Potsaid, V. Jayaraman, J. Jiang, J. G. Fujimoto, A. E. Cable, Opt. Lett. 2013, 38, 673.
[18] T. Klein, W. Wieser, C. M. Eigenwillig, B. R. Biedermann, R. Huber, Opt. Express 2011, 19, 3044.
[19] M. Bonesi, M. Minneman, J. Ensher, B. Zabihian, H. Sattmann, P. Boschert, E. Hoover, R. Leitgeb, M. Crawford, W. Drexler, Opt. Express 2014, 22, 2632.
[20] Z. Wang, B. Potsaid, L. Chen, C. Doerr, H.-C. Lee, T. Nielson, V. Jayaraman, A. E. Cable, E. Swanson, J. G. Fujimoto, Optica 2016, 3, 1496.
[21] Y. Jia, O. Tan, J. Tokayer, B. Potsaid, Y. Wang, J. J. Liu, M. F. Kraus, H. Subhash, J. G. Fujimoto, J. Hornegger, D. Huang, Opt. Express 2012, 20, 4710.
[22] B. Baumann, B. Potsaid, M. F. Kraus, J. J. Liu, D. Huang, J. Hornegger, A. E. Cable, J. S. Duker, J. G. Fujimoto, Biomed. Opt. Express 2011, 2, 1539.
[23] S. Song, J. Xu, S. Men, T. T. Shen, R. K. Wang, J. Biophoton. 2017, 10, 1398.
[24] Y. Ling, Y. Gan, X. Yao, C. P. Hendon, Opt. Lett. 2017, 42, 1333.
[25] J. Sun, S. J. Lee, L. Wu, M. Samtinoranont, H. Xie, Opt. Express 2012, 20, 1084.
[26] W. Drexler, J. G. Fujimoto, Optical Coherence Tomography: Technology and Applications, Springer, Berlin, Germany 2015.
[27] G. Liu, W. Qi, L. Yu, Z. Chen, Opt. Express 2011, 19, 3657.
[28] W. Choi, B. Potsaid, V. Jayaraman, B. Baumann, I. Grulkowski, J. J. Liu, C. D. Lu, A. E. Cable, D. Huang, J. S. Duker, J. G. Fujimoto, Opt. Lett. 2013, 38, 338.
[29] N. G. Horton, K. Wang, D. Kobat, C. G. Clark, F. W. Wise, C. B. Schaffer, C. Xu, Nat. Photon. 2013, 7, 205.
[30] C. O. Yanez, A. R. Morales, X. Yue, T. Urakami, M. Komatsu, T. A. Jarvinen, K. D. Belfield, PLoS One 2013, 8, e67559.
[31] J. A. Jensen, Estimation of Blood Velocities Using Ultrasound: A Signal Processing Approach, Cambridge University Press, Cambridge, United Kingdom 1996.
[32] J. M. Schmitt, S. Xiang, K. M. Yung, J. Biomed. Opt. 1999, 4, 95.
[33] M. D. Kulkarni, T. G. van Leeuwen, S. Yazdanfar, J. A. Izatt, Opt. Lett. 1998, 23, 1057.
[34] S. Yazdanfar, C. Yang, M. V. Sarunic, J. A. Izatt, Opt. Express 2005, 13, 410.
[35] S. A. Boppart, S. A. Boppart, M. E. Brezinski, C. Pitris, C. Pitris, J. G. Fujimoto, Neurosurgery 1998, 43, 834.

What is claimed is:

1. A non-transitory computer-accessible medium having stored thereon computer-executable instructions for generating at least one image of at least one three-dimensional (3D) anatomical flow map, wherein, when a computer arrangement executes the instructions, the computer arrangement is configured to perform procedures comprising:
receiving at least one optical coherence tomography (OCT) signal comprising a plurality of A-scans;
splitting the at least one OCT signal into a plurality of subspectra, wherein a bandwidth for a particular one of the subspectra is a total bandwidth of the at least one OCT signal minus an amount of bandwidth lost based on a number of the subspectra;
for each subspectra, determine a Doppler phase difference between subsequent A-scans;

determining a Doppler phase difference for the OCT signal by averaging the plurality of Doppler phase differences between subsequent A-scans determined for each subspectra; and generating the at least one image of the at least one 3D anatomical flow map based on the Doppler phase difference for the OCT signal.

2. The computer-accessible medium of claim 1, wherein the at least one OCT signal is a swept-source OCT signal.

3. The computer-accessible medium of claim 1, wherein computer arrangement is configured to split the at least one OCT signal into the subspectra based on a Hamming window.

4. The computer-accessible medium of claim 3, wherein the computer arrangement is further configured to optimize the Hamming distance window to minimize a nearest side lobe for each of the subspectra.

5. The computer-accessible medium of claim 1, wherein the computer arrangement is further configured to shift a position of at least one of the subspectra prior to averaging the subspectra.

6. The computer-accessible medium of claim 5, wherein the computer arrangement is configured to shift the position of all but one of the subspectra prior to averaging the subspectra.

7. The computer-accessible medium of claim 5, wherein an amount of the shift is based on a number of the subspectra.

8. The computer-accessible medium of claim 5, wherein the computer arrangement is configured to shift the position such that each of the subspectra has a same position.

9. The computer-accessible medium of claim 1, wherein the computer arrangement is configured to split the at least one OCT signal by shifting a filter across the at least one OCT signal using a particular step size.

10. The computer-accessible medium of claim 9, wherein the particular step size is an amount of bandwidth lost based on a number of the subspectra divided by a total number of the sub spectra.

11. The computer-accessible medium of claim 1, wherein the at least one image includes a blood flow.

12. The computer-accessible medium of claim 1, wherein the at least one OCT signal includes at least two OCT signals, and wherein the computer arrangement is configured to:
split a first OCT signal of the at least two OCT signals into a plurality of first subspectra;
split a second OCT signal of the at least two OCT signals into a plurality of second subspectra;
generate a subspectra set by subtracting the first subspectra from the second subspectra; and
generate the at least one image of the at least one 3D anatomical flow map based on the subspectra set.

13. The computer-accessible medium of claim 12, wherein the computer arrangement is further configured to generate an average of the subspectra set.

14. The computer-accessible medium of claim 13, wherein the computer arrangement is configured to generate the at least one image based on the averaged subspectra set.

15. A system for generating at least one image of at least one three-dimensional (3D) anatomical flow map, comprising:
a computer hardware arrangement configured to:
receive at least one optical coherence tomography (OCT) signal comprising a plurality of A-scans;
split the at least one OCT signal into a plurality of subspectra; wherein a bandwidth for a particular one of the subspectra is a total bandwidth of the at least one OCT signal minus an amount of bandwidth lost based on a number of the subspectra;
for each subspectra, determine a Doppler phase difference between subsequent A-scans;
determining a Doppler phase difference for the OCT signal by averaging the plurality of Doppler phase differences between subsequent A-scans determined for each subspectra; and
generate the at least one image of the at least one 3D anatomical flow map based on the Doppler phase difference for the OCT signal.

16. The system of claim 15, wherein the at least one OCT signal includes at least two OCT signals, and wherein the computer hardware arrangement is configured to:
split a first OCT signal of the at least two OCT signals into a plurality of first subspectra;
split a second OCT signal of the at least two OCT signals into a plurality of second subspectra;
generate a subspectra set by subtracting the first subspectra from the second subspectra; and
generate the at least one image of the at least one 3D anatomical flow map based on the subspectra set.

17. The system of claim 16, wherein the computer hardware arrangement is configured to generate an average of the subspectra set, wherein the at least one image is based on the averaged subspectra set.

18. A method for generating at least one image of at least one three-dimensional (3D) anatomical flow map, comprising:
receiving at least one optical coherence tomography (OCT) signal comprising a plurality of A-scans;
splitting the at least one OCT signal into a plurality of subspectra wherein a bandwidth for a particular one of the subspectra is a total bandwidth of the at least one OCT signal minus an amount of bandwidth lost based on a number of the subspectra;
for each sub spectra, determining a Doppler phase difference between subsequent A-scans;
determining a Doppler phase difference for the OCT signal by averaging the plurality of Doppler phase differences between subsequent A-scans determined for each subspectra; and
using a computer hardware arrangement, generating the at least one image of the at least one 3D anatomical flow map based on the Doppler phase difference for the OCT signal.

19. The method of claim 18, wherein the at least one OCT signal includes at least two OCT signals, and further comprising:
splitting a first OCT signal of the at least two OCT signals into a plurality of first subspectra;
splitting a second OCT signal of the at least two OCT signals into a plurality of second subspectra;
generating a subspectra set by subtracting the first subspectra from the second subspectra; and
generating the at least one image of the at least one 3D anatomical flow map based on the subspectra set.

20. The method of claim 19, wherein the generating of the image includes generating an average of the subspectra set and wherein the image is based on the averaged subspectra set.

21. A non-transitory computer-accessible medium having stored thereon computer-executable instructions for generating at least one image of at least one three-dimensional (3D) anatomical flow map, wherein, when a computer arrangement executes the instructions, the computer arrangement is configured to perform procedures comprising:
- receiving at least one optical coherence tomography (OCT) signal;
- splitting the at least one OCT signal into a plurality of subspectra by shifting a filter across the at least one OCT signal using a step size related to an amount of bandwidth lost based on a number of the subspectra divided by a total number of the subspectra; and
- generating the at least one image of the at least one 3D anatomical flow map based on the averaged subspectra.

* * * * *

UNITED STATES PATENT AND TRADEMARK OFFICE
CERTIFICATE OF CORRECTION

| | |
|---|---|
| PATENT NO. | : 11,771,321 B2 |
| APPLICATION NO. | : 16/755702 |
| DATED | : October 3, 2023 |
| INVENTOR(S) | : Yingtian Pan, Wei Chen and Congwu Du |

It is certified that error appears in the above-identified patent and that said Letters Patent is hereby corrected as shown below:

On the Title Page

(73) Assignee, please delete "SUNY" and substitute "the State University of New York" therefore.

In the Claims

In Claim 3, Column 19, Line 11, insert --the-- before -computer-.

In Claim 10, Column 19, Line 39, delete "sub spectra" and substitute "subspectra" therefore.

Signed and Sealed this
Fifth Day of March, 2024

Katherine Kelly Vidal
*Director of the United States Patent and Trademark Office*